United States Patent
Mazed et al.

(10) Patent No.: US 8,017,147 B2
(45) Date of Patent: Sep. 13, 2011

(54) NUTRITIONAL SUPPLEMENT FOR THE PREVENTION OF CARDIOVASCULAR DISEASE, ALZHEIMER'S DISEASE, DIABETES, AND REGULATION AND REDUCTION OF BLOOD SUGAR AND INSULIN RESISTANCE

(76) Inventors: Mohammad A. Mazed, Yorba Linda, CA (US); Sayeeda Mazed, Yorba Linda, CA (US)

( * ) Notice: Subject to any disclaimer, the term of this patent is extended or adjusted under 35 U.S.C. 154(b) by 0 days.

(21) Appl. No.: 12/573,012

(22) Filed: Oct. 2, 2009

(65) Prior Publication Data
US 2010/0021533 A1    Jan. 28, 2010

Related U.S. Application Data

(63) Continuation-in-part of application No. 12/390,302, filed on Feb. 20, 2009, now abandoned, which is a continuation-in-part of application No. 12/169,523, filed on Jul. 8, 2008, now abandoned.

(60) Provisional application No. 61/043,059, filed on Apr. 7, 2008, provisional application No. 61/274,306, filed on Aug. 14, 2009.

(51) Int. Cl.
| A61K 36/00 | (2006.01) |
|---|---|
| A61K 36/9066 | (2006.01) |
| A61K 36/25 | (2006.01) |
| A61K 36/58 | (2006.01) |
| A61K 36/234 | (2006.01) |
| A61K 36/734 | (2006.01) |
| A61K 36/704 | (2006.01) |
| A61K 36/539 | (2006.01) |
| A61K 35/20 | (2006.01) |
| A61K 38/43 | (2006.01) |
| A61K 9/14 | (2006.01) |
| A61K 36/906 | (2006.01) |
| A61K 36/254 | (2006.01) |
| A61K 36/54 | (2006.01) |
| A61K 36/736 | (2006.01) |

(52) U.S. Cl. ....... 424/450; 424/725; 424/535; 424/94.1; 424/489; 424/756; 424/728; 424/739; 424/735; 977/773; 977/907; 977/915; 977/926

(58) Field of Classification Search .................. None
See application file for complete search history.

(56) References Cited

U.S. PATENT DOCUMENTS

| 5,976,568 | A | * | 11/1999 | Riley | ............ | 424/451 |
|---|---|---|---|---|---|---|
| 6,551,629 | B1 | * | 4/2003 | Gorsek | ............ | 424/725 |
| 2002/0164388 | A1 | * | 11/2002 | Sosnowski et al. | ............ | 424/752 |
| 2005/0163873 | A1 | * | 7/2005 | Ritch | ............ | 424/752 |

FOREIGN PATENT DOCUMENTS

CN    1994362 A    *   7/2007

OTHER PUBLICATIONS

Calabro et al, The rutin/beta-cyclodextrin interactions in fully aqueous solution: spectroscopic studies and biological assays, Journal of pharmaceutical and biomedical analysis, (Jan. 4, 2005) vol. 36, No. 5, pp. 1019-1027.*

Ohnishi et al, Chemical composition of lipids, especially triacylglycerol, in grape seeds, Agricultural and Biological Chemistry (1990) vol. 54, No. 4, pp. 1035-1042.*

\* cited by examiner

*Primary Examiner* — Qiuwen Mi

(57) ABSTRACT

A synergistic mixture (which may be utilized as a food or a drink or a supplement or a drug or a cosmetic or a hygienic product) that is formulated and is capable of improving a person's well being, lowering the risks of cardiovascular and/or Alzheimer's diseases and/or lowering blood sugar using natural and synthetic ingredients. Numerous ratios may be formulated for aroma, color, flavor, flow (viscosity), taste and uniformity. Moreover, ingredients for sugar substitutes, natural preservatives, nano-dispersion, nano-emulsion, nano-encapsulation of ingredients and apparatus for personalized nutrition are also described herein.

2 Claims, 14 Drawing Sheets

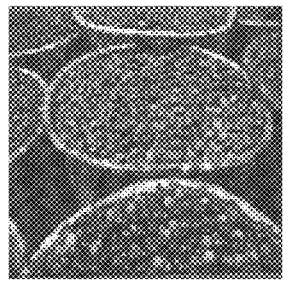
Figure A-1
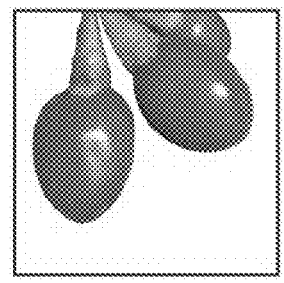
Figure A-2
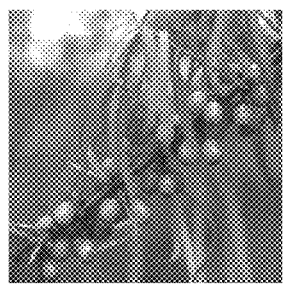
Figure A-3
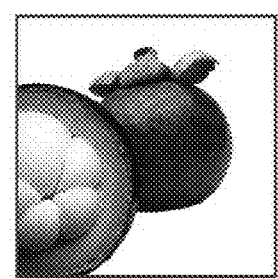
Figure A-4
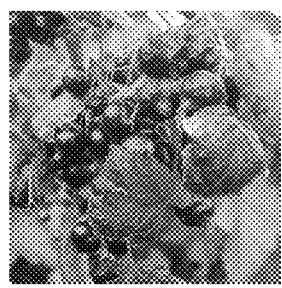
Figure A-5
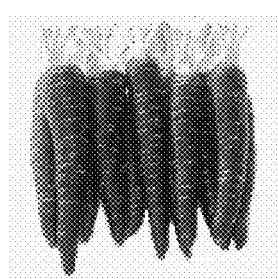
Figure A-6
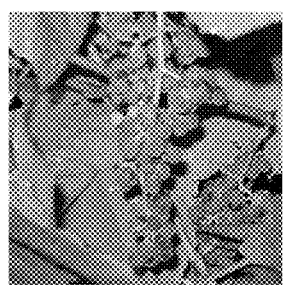
Figure A-7
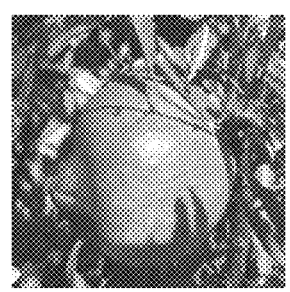
Figure A-8

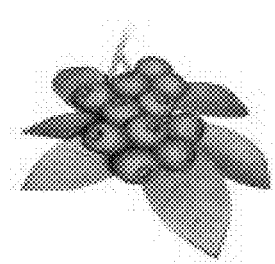
Figure A-9
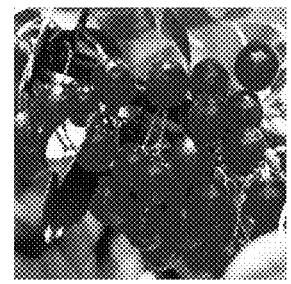
Figure A-10
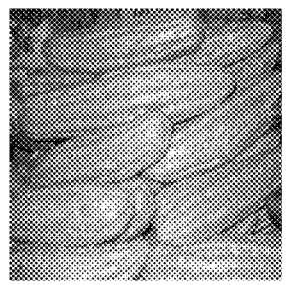
Figure A-11
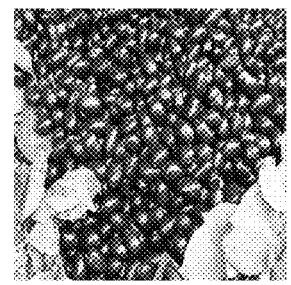
Figure A-12
Figure A-13
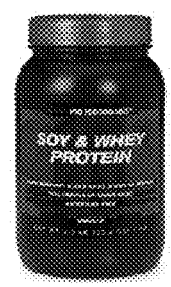
Figure A-14
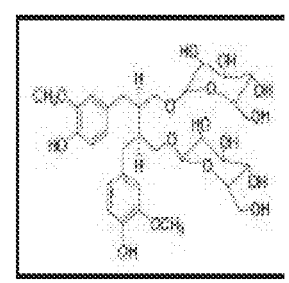
Figure A-15
Figure A-16

Figure A-17
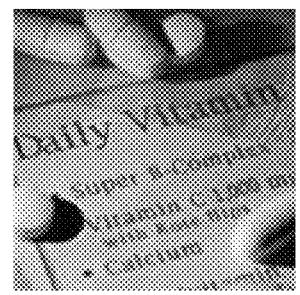
Figure A-18
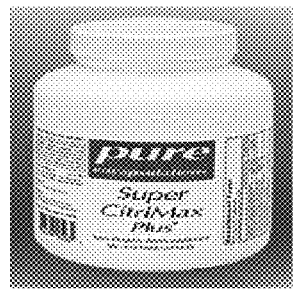
Figure A-19
Figure A-20
Figure A-21
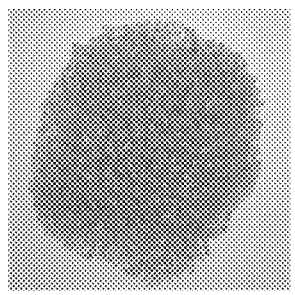
Figure A-22
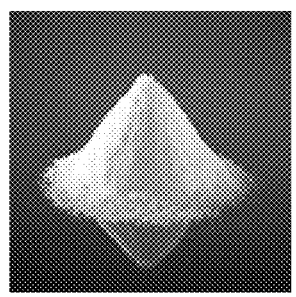
Figure A-23

Figure B-1
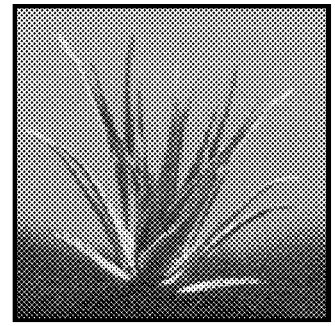
Figure B-2
Figure B-3
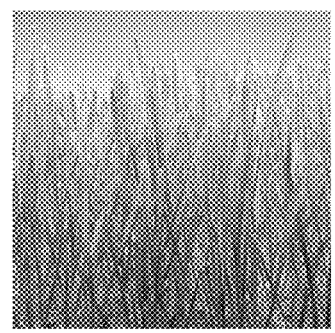
Figure B-4
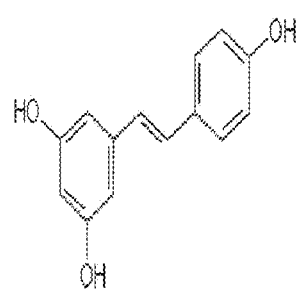
Figure B-5
Figure B-6

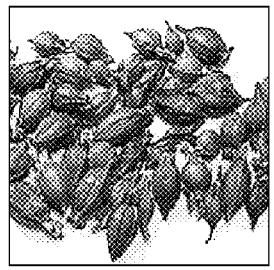
Figure C-1
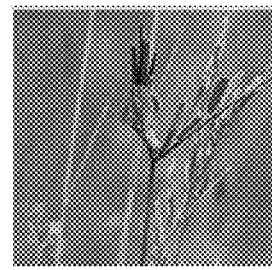
Figure C-2
Figure C-3
Figure C-4
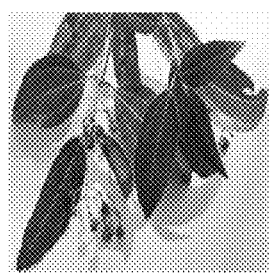
Figure C-5
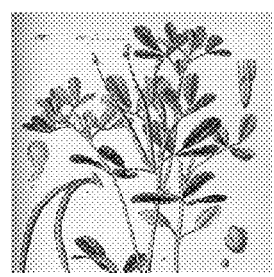
Figure C-6
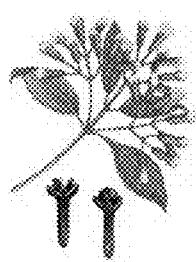
Figure C-7
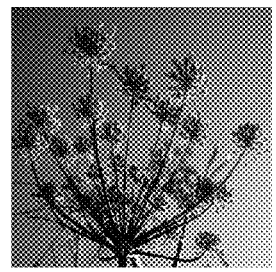
Figure C-8

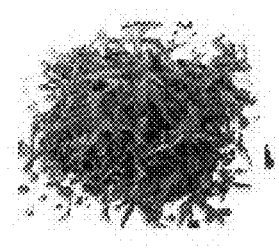
Figure D-1
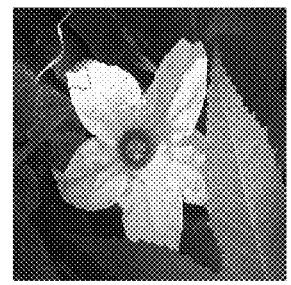
Figure D-2
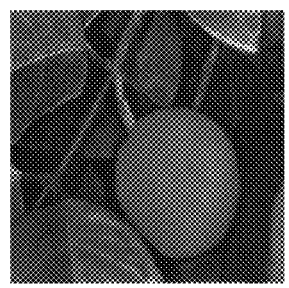
Figure D-3
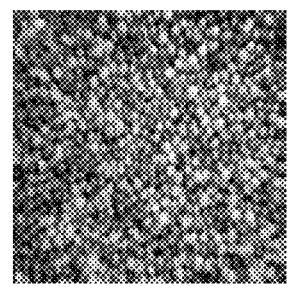
Figure D-4
Figure D-5
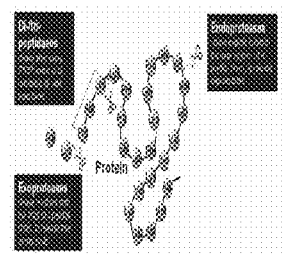
Figure D-6
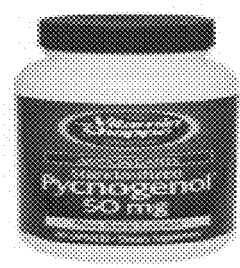
Figure D-7
Figure D-8

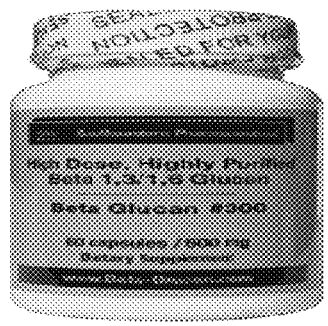
Figure D-9
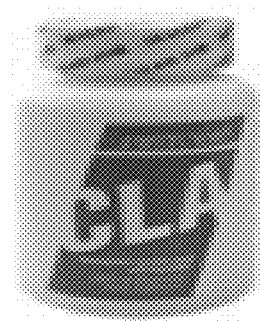
Figure D-10
Figure D-11
Figure D-12

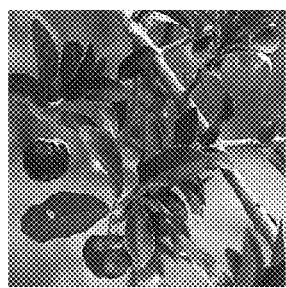
Figure E-1
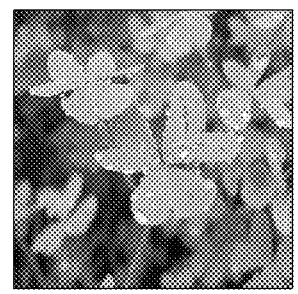
Figure E-2
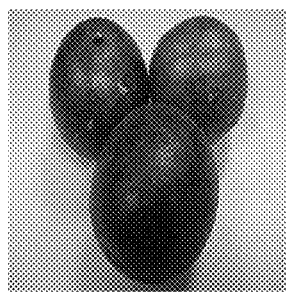
Figure E-3
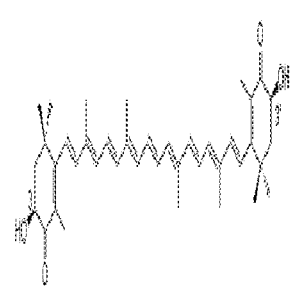
Figure E-4
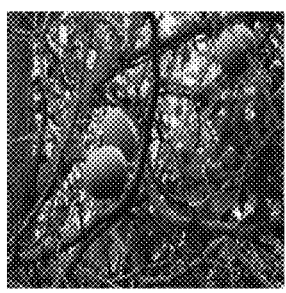
Figure E-5
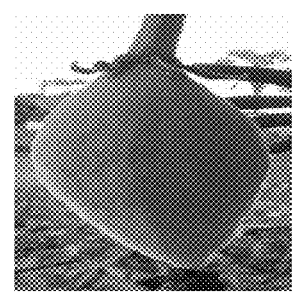
Figure E-6
Figure E-7
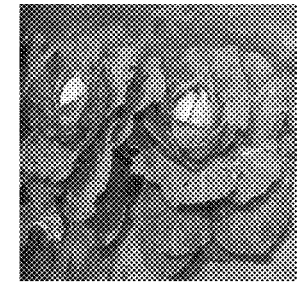
Figure E-8

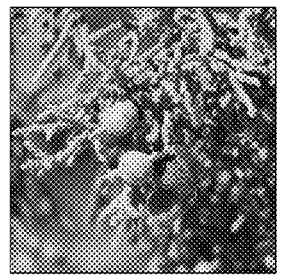
Figure E-9
Figure E-10
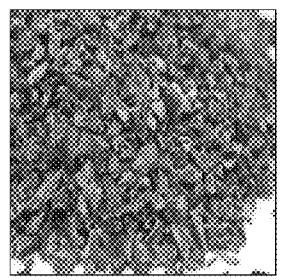
Figure E-11
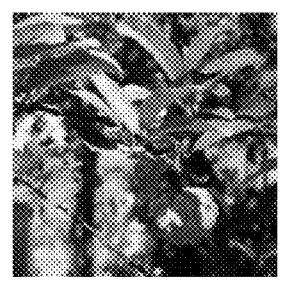
Figure E-12
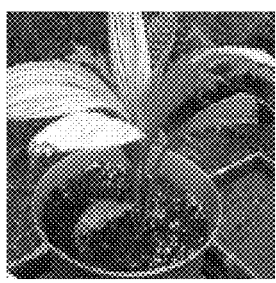
Figure E-13
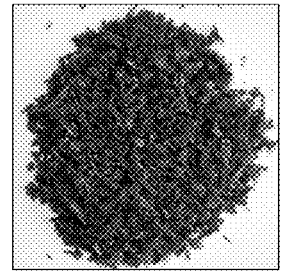
Figure E-14
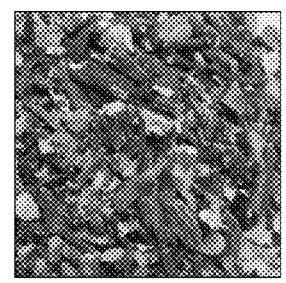
Figure E-15
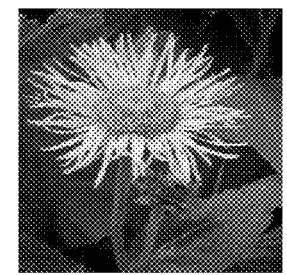
Figure E-16

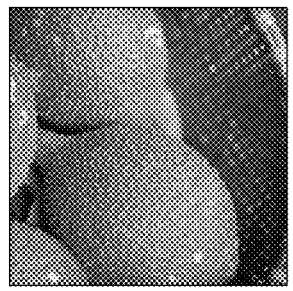
Figure E-17
Figure E-18
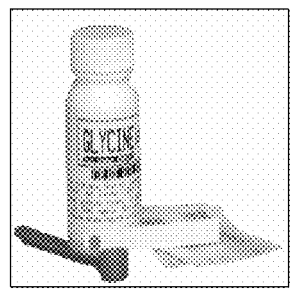
Figure E-19
Figure E-20
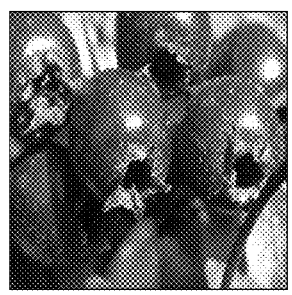
Figure E-21
Figure E-22
Figure E-23
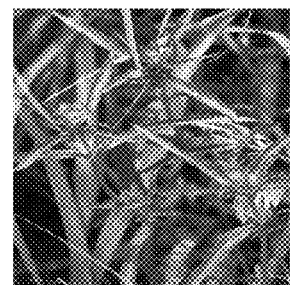
Figure E-24

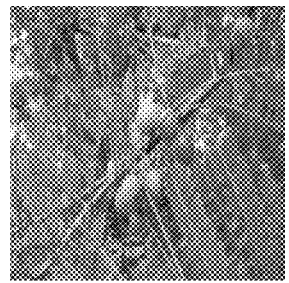
Figure E-25
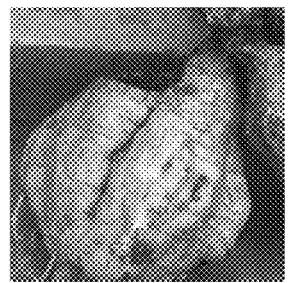
Figure E-26
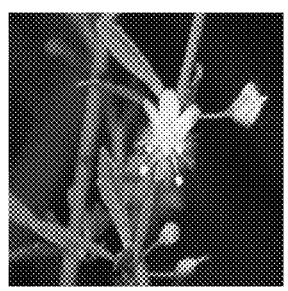
Figure E-27
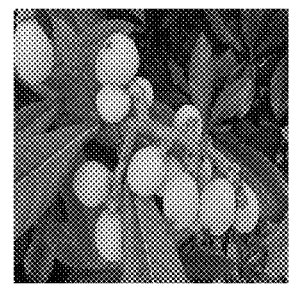
Figure E-28
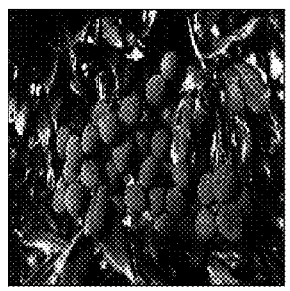
Figure E-29
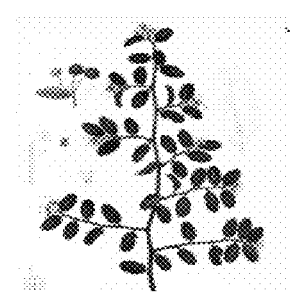
Figure E-30
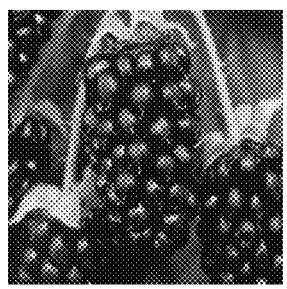
Figure E-31
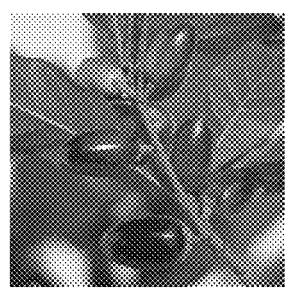
Figure E-32

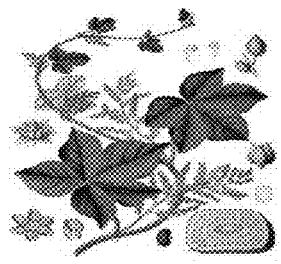
Figure E-33
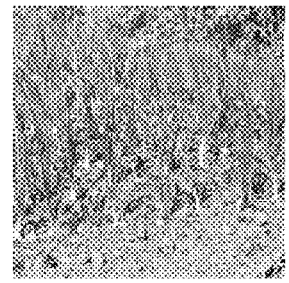
Figure E-34
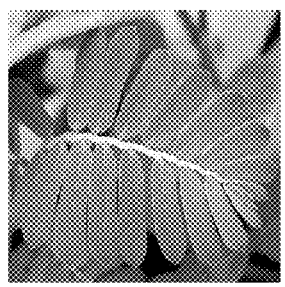
Figure E-35
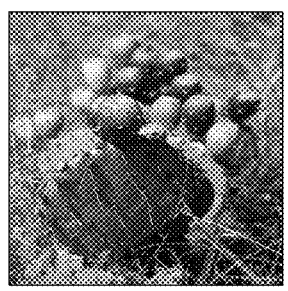
Figure E-36
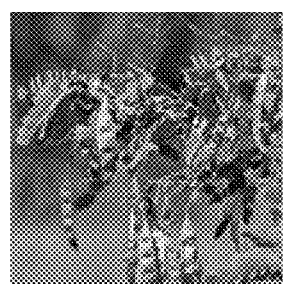
Figure E-37
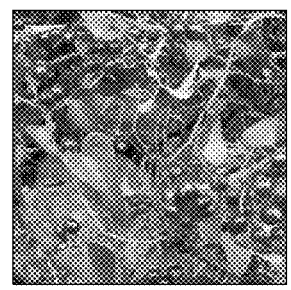
Figure E-38
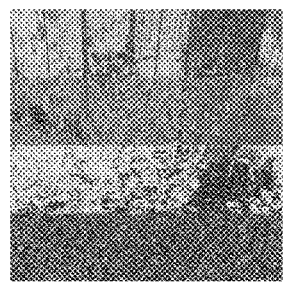
Figure E-39
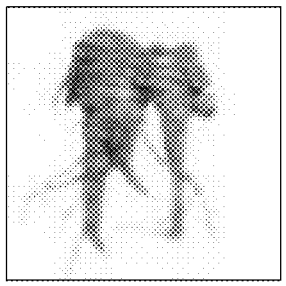
Figure E-40

Figure E-41
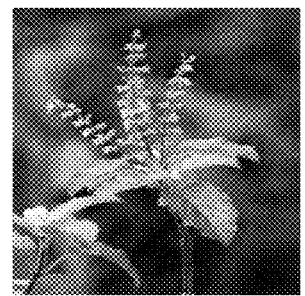
Figure E-42
Figure E-43
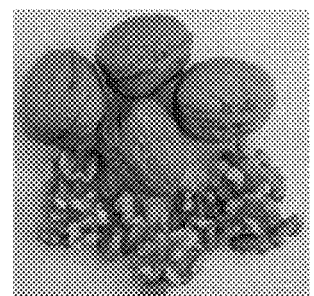
Figure E-44

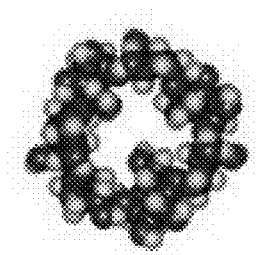
Figure F-1
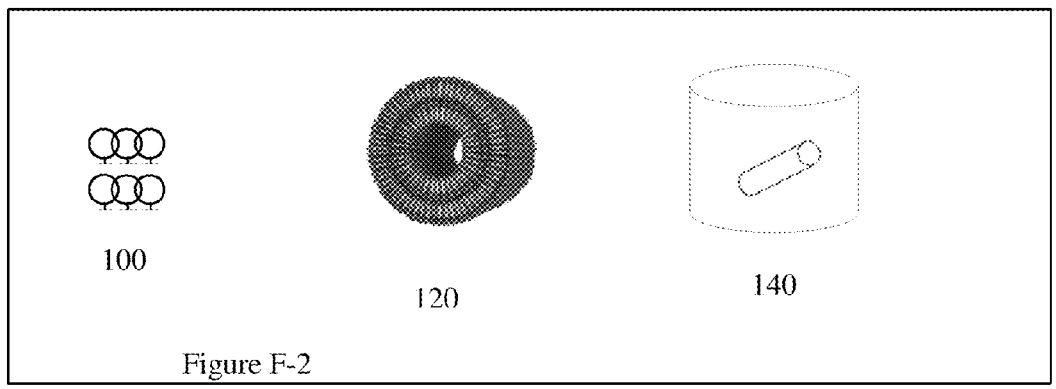
100  120  140
Figure F-2
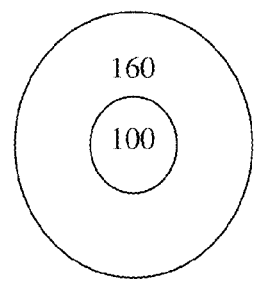
Figure F-3
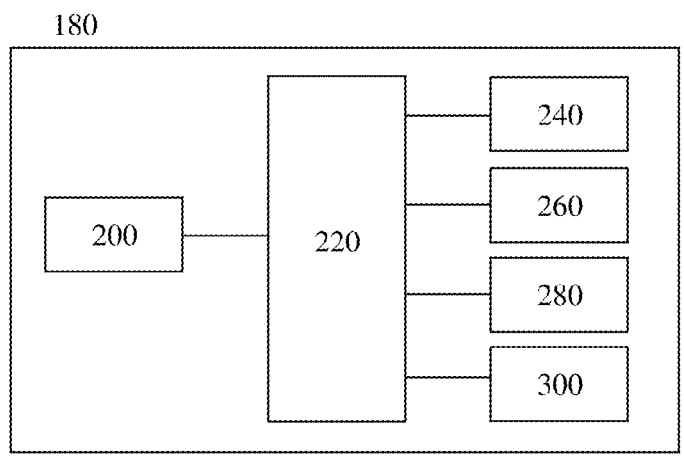
Figure F-4

NUTRITIONAL SUPPLEMENT FOR THE PREVENTION OF CARDIOVASCULAR DISEASE, ALZHEIMER'S DISEASE, DIABETES, AND REGULATION AND REDUCTION OF BLOOD SUGAR AND INSULIN RESISTANCE

CROSS REFERENCE OF RELATED APPLICATIONS

The present application is a continuation-in-part of and claims priority to U.S. Nonprovisional patent application Ser. No. 12/390,302, entitled, "Nutritional Supplement For The Prevention Of Cardiovascular Disease, Alzheimer's Disease, Diabetes, and Regulation and Reduction of Blood Sugar and Insulin Resistance," filed on Feb. 20, 2009 (now abandoned), which is a continuation-in-part of U.S. Nonprovisional patent application Ser. No. 12/169,523, entitled "A Nutritional Supplement for the Prevention of Cardiovascular Disease, Alzheimer's Disease, Diabetes and Regulation and Reduction of Blood Sugar and Insulin Resistance," filed on Jul. 8, 2008 (now abandoned), which claims priority to U.S. Provisional Patent Application No. 61/043,059, entitled "A Nutritional Supplement to Aid in the Regulation and Reduction of Blood Sugar," filed on Apr. 7, 2008. The present application is also related to and claims priority of U.S. Provisional Patent Application No. 61/274,306, filed on Aug. 14, 2009. All of these patent applications are incorporated herein by reference.

BACKGROUND OF THE INVENTION

1. Field of Invention

The present invention relates to synergetic (a mixture of super nutrients, anti-oxidants and anti-degenerative elements adequately balanced with other essential micro-nutrients to enhance synergy) formulation, molecular nutrition, nano-dispersion, nano-emulsion, nano-encapsulation and nutragenomics.

2. Discussion of the Related Art

Many studies suggest that blood cholesterol levels may be an important risk factor for Alzheimer's disease. If blood flow is restricted because of a buildup of plaque or clots in the blood vessels, or if blood becomes too viscous for smooth flow, less oxygen gets to the brain cells and fewer waste residues leave the brain cells. Evidence also suggests a link between cardiovascular-related conditions and dementia. One of the most intriguing recent discoveries is that many risk factors for cardiovascular, Type-1 and Type-2 diabetic diseases are also risk factors for Alzheimer's disease.

Diabetes is closely linked to, in the early stage, metabolic syndrome, and on the later stage obesity, hence, a new quasi-medical term—diabesity. Because of diabesity, there are macrophages in fat tissues. These macrophages produce "cytokine" molecules. These "cytokine" molecules can cause inflammation in the heart and islets of the pancreas hence increase the insulin resistance in muscle and liver tissues. Diabetes is a disease condition where the body does not produce enough or properly use insulin, a hormone needed to convert glucose, carbohydrates and others into energy needed for daily life. Diabetes is marked by high levels of blood glucose resulting from defects in insulin production and/or insulin action. As the need for insulin rises, the pancreas gradually loses its ability to produce it. Diabetes can lead to serious complications, from kidney disease, high blood pressure, stroke and premature death, but people with diabetes can take steps to control the disease and lower the risk of complications.

Currently, there are approximately 250 million people worldwide living with Type-1 and Type-2 diabetes. The primary causes of diabetes are (1) genetic make-up (2) sedentary lifestyles and (3) dietary habits.

Presently, the known remedies for Type-2 diabetes are: (1) weight/fat reduction, (2) appropriate food, drink and nutritional supplement consumption, (3) stress reduction and (4) smoking cessation.

Bioactive compounds (molecular nutrients) are occurring in small quantities in a seed or a root or a rhizome or a leaf or a fruit or fruit skin or a vegetable or a vegetable skin or plant bark. There is epidemiologic evidence demonstrating a protective role of these bioactive compounds (molecular nutrients) to prevent and/or delay cardiovascular, Type-2 diabetes and/or Alzheimer's diseases.

SUMMARY OF THE INVENTION

A liquid mixture is formulated to improve a person's well being, with possible implications to lowering the risks of cardiovascular and/or Alzheimer's diseases and/or lowering blood sugar using natural ingredients. A mixture of the present invention may be used as a food or a drink or a supplement or a drug or a cosmetic or a hygienic product. Numerous ratios may be formulated for aroma, color, flavor, flow (viscosity), taste and uniformity. The liquid mixture may be diluted with water and/or skimmed milk.

The present invention is better understood upon consideration of the examples below in conjunction with the drawings.

BRIEF DESCRIPTION OF THE DRAWINGS

FIG. A-1 shows examples of Acaiberry (i.e., *Euterpe oleracea*).

FIG. A-2 shows examples of Goji or Wolfberry (i.e., *Lycium barbarum*).

FIG. A-3 shows examples of Seaberry (i.e., *Hippophae rhamnoides*).

FIG. A-4 shows examples of Mangosteen (i.e., *Garcinia mangostana*).

FIG. A-5 shows examples of Black Currant (i.e., *Ribes nigrum*).

FIG. A-6 shows examples of Black Carrot (i.e., *Daucus carota*).

FIG. A-7 shows examples of Grape (i.e., *Vitis vinifera, Vitis labrusca, Vitis rotundifolia*).

FIG. A-8 shows an example of a Pomegranate (i.e., *Punica granatum*).

FIG. A-9 shows examples of Blueberry (i.e., *Vaccinium* spp.—*Vaccinium angustifolium, Vaccinium boreale, Vaccinium caesariense*).

FIG. A-10 shows an example of Tart Cherry (i.e., *Prunus cerasus*).

FIG. A-11 shows examples of Bitter Melon (i.e., *Momordica charantia*) (Synonyms: *Momordica chinensis, Momordica elegans, Momordica indica, Momordica operculata, Momordica sinensis, Sicyos fauriei*).

FIG. A-12 shows examples of Jamun (i.e, *Syzygium cumini*).

FIG. A-13 shows examples of Tumeric Plant (i.e., *Curcuma longa*).

FIG. A-14 shows a bottle of commercially available Whey, Soy or Rapeseed Protein.

FIG. A-15 shows a molecule of Secoisolariciresinol Diglycoside (SDG) lignans.

FIG. A-16 shows a bottle of commercially available Salba Extract (i.e., *Salvia hispanica*).

FIG. A-17 shows examples of sprouted Flaxseed (i.e., *Linum usitatissimum*).

FIG. A-18 shows examples of commercially available Micro-nutrients pills.

FIG. A-19 shows a bottle of commercially available Super CitriMax®.

FIG. A-20 shows a bottle of commercially available Hydroxy Citric Acid (HCA).

FIG. A-21 shows a bottle of commercially available L-Carnitine.

FIG. A-22 shows an example of Fenugreek Gum.

FIG. A-23 shows an example of commercially available Erythritol.

FIG. B-1 shows a bottle of commercially available Grape Seed extract (i.e., *Vitis vinifera, Vitis rotundifolia, Vitis labrusca*).

FIG. B-2 shows an example of an *Aloe Vera* plant (i.e., *Aloe vera*).

FIG. B-3 shows an example of an Orange Peel (Citrus sinensis).

FIG. B-4 shows an example of Wheat Grass (i.e., *Triticum aestivum*).

FIG. B-5 shows a molecule of Resveratrol or Resvida® or Resvenox®

FIG. B-6 shows a bottle of commercially available Piracetam®.

FIG. C-1 shows an example of Gardenia (i.e., *Gardenia jasminoides*).

FIG. C-2 shows an example of an Indian Kino tree (i.e., *Pterocarpus marsupium*).

FIG. C-3 shows an example of a Guduchi plant (i.e., *Tinospora cordifolia*).

FIG. C-4 shows an example of a Gurmar or Periploca of the Woods plant (i.e., *Gymnema sylvestre*).

FIG. C-5 shows an example of a Cinnamon plant (i.e., *Cinnamomum zeylanicum, Cinnamomum cassia blume*).

FIG. C-6 shows an example of a Fenugreek plant (i.e., *Trigonella foenum-graecum*).

FIG. C-7 shows an example of a Clove plant (i.e., *Syzygium aromaticum*).

FIG. C-8 shows an example of a Fennel plant (i.e., *Foeniculum vulgare*).

FIG. D-1 shows Decaffeinated Black, Green and White (i.e., *Camellia sinensis*).

FIG. D-2 shows an example of Ivy Gourd flower (i.e., *Coccinia indica*).

FIG. D-3 shows a *Salacia* fruit (i.e., *Salacia oblonga*).

FIG. D-4 shows an example of Resistant starch.

FIG. D-5 shows a box of commercially available Diachrome™.

FIG. D-6 shows a box of commercially available InsuVital™.

FIG. D-7 shows a bottle of commercially available Pycnogenol®—a bark extract of pine tree.

FIG. D-8 shows a bottle of a commercially available Biotin.

FIG. D-9 shows an example of a commercially available Beta-glucan.

FIG. D-10 shows a bottle of commercially available Conjugated Linoleum Acid (CLA).

FIG. D-11 shows a bottle of commercially available Alpha-Lipoic acid (ALA).

FIG. D-12 shows a bottle of commercially available SX-fraction.

FIG. E-1 shows examples of Acerolaberry (i.e., *Maldighia glabra*).

FIG. E-2 shows an example of Alfalfa (i.e., *Medicago sativa*).

FIG. E-3 shows examples of Arhat (i.e., *Siraitia grosvenorii*).

FIG. E-4 shows an example of Astaxanthin.

FIG. E-5 shows an example of Bael (i.e., *Aegle marmelos*).

FIG. E-6 shows an example of Baobab (i.e., *Adansonia digitata*).

FIG. E-7 shows an example of Oubli (i.e., *Pentadiplandra brazzeana*) from which both Bazzein & Pentadin proteins are extracted.

FIG. E-8 shows an example of Cabbage (i.e., *Brassica oleracea*).

FIG. E-9 shows examples of Cedarberry (i.e., *Juniperus monosperma*).

FIG. E-10 shows an example of Chongcao (i.e., *Cordyceps sinensis*).

FIG. E-11 shows an example of Cocoa Extract (i.e., *Theobroma cacao*).

FIG. E-12 shows examples of Custard Apple Leaf (i.e., *Annona reticulata*).

FIG. E-13 shows an example of Curculin.

FIG. E-14 shows an example of Damiana Extract (i.e., *Turnera diffusa*).

FIG. E-15 shows an example of Dandelion Root (i.e., *Taraxacum officinale*).

FIG. E-16 shows an example of Elecampane Leaf (i.e., *Inula helenium*).

FIG. E-17 shows an example of Gac (i.e., *Momordica cochinchinensis*).

FIG. E-18 shows examples of Ginsengberry (i.e., *Panax quinquefolium*).

FIG. E-19 shows an example of Glycine.

FIG. E-20 shows an example of commercially available Guar Gum (i.e., *Cyamopsis tetragonolobus*).

FIG. E-21 shows examples of Hawthorneberry (i.e., *Crataegus oxyacantha*).

FIG. E-22 shows an example of Huereque (i.e., *Ibervillea sonorae*).

FIG. E-23 shows an example of Indian Beech (i.e., *Pongamia pinnata*).

FIG. E-24 shows an example of Indian Gentian (i.e., *Swertia chirata*).

FIG. E-25 shows an example of Indian Gooseberry (i.e., *Phyllanthus emblica*).

FIG. E-26 shows an example of Kudzu (i.e., *Pueraria lobata, Pueraria thomsonii*).

FIG. E-27 shows an example of Licorice Weed (i.e., *Scoparia dulcis*) (Synonyms: *Scoparia grandiflora, Scoparia ternata, Capraria dulcis, Gratiola micrantha*).

FIG. E-28 shows examples of Loquats (i.e., *Eriobotrya japonica*).

FIG. E-29 shows an example of Lychee (i.e., *Litchi chinensis*).

FIG. E-30 shows an example of Mabinlin (i.e., *Capparis masaikai*).

FIG. E-31 shows examples of Marionberry (i.e., *Rubus ursinus*).

FIG. E-32 shows an example of Miraculin (i.e., *Synsepalum dulcificum* or *Richadella dulcifica*).

FIG. E-33 shows an example of Monellin (i.e., *Dioscoreophyllum cumminsii*).

FIG. E-34 shows examples from the Onion Family (i.e., Onion, Garlic, Scallion and Leeks) Liliaceae Family.

FIG. E-35 shows an example of a Phyllanthus Plant (i.e., *Phyllanthus niruri*).

FIG. E-36 shows an example of Prickly Pear (i.e., *Opuntia ficus-indica*).

FIG. E-37 shows an example of Ranawara or Avaram (i.e., *Cassia auriculata*).

FIG. E-38 shows an example of Sarsaparilla (i.e., *Smilax officinalis*).

FIG. E-39 shows an example of Stevia (i.e., *Stevia rebaudiana*).

FIG. E-40 shows examples of Suma Root (i.e., *Pfaffia paniculata*).

FIG. E-41 shows an example of Thaumatin (i.e., *Thaumatococcus danieli*).

FIG. E-42 shows an example of Tulsi (i.e., *Ocimum sanctum, Ocimum tenuiflorum*).

FIG. E-43 shows an example of Water Hyssop (i.e., *Bacopa Monnieri*).

FIG. E-44 shows examples of Walnut (i.e., *Juglans regia*).

FIG. F-1 shows an example of Cyclodextrin.

FIG. F-2 shows an example of encapsulation of an ingredient in a nano-tube.

FIG. F-3 shows a method of encapsulation of an ingredient in a nano-particle.

FIG. F-4 shows an example of an apparatus for personalized nutrition.

DETAILED DESCRIPTION OF THE PREFERRED EMBODIMENTS

Each of the following examples is a liquid mixture that is formulated for and believed to be effective for improving a person's well being, lowering the risks of cardiovascular, and/or Alzheimer's diseases and/or lowering blood sugar.

Example 1

Mixture A

A mixture including the following ingredients:

| Acaiberry | mL | 30 |
|---|---|---|
| Gojiberry/Wolfberry | mL | 30 |
| Seaberry &/or Mangosteen | mL | 30 |
| Black Currant &/or Black Carrot | mL | 30 |
| Grape: Concord and/or Red Muscadine | mL | 30 |
| Pomegranate | mL | 30 |
| Blueberry | mL | 30 |
| Red Tart Cherry | mL | 20 |
| Bitter Melon &/or Jamun | mL | 20 |
| Curcumin Extract Powder | Mg | 25 |
| Protein(s): Whey &/or Soy &/or Rapeseed | G | 05 |
| SDG &/or Salba &/or Sprouted Flaxseed | G | 01 |
| Vitamin A | IU | 1000 |
| Vitamin $B_3$ | Mg | 15 |
| Vitamin $B_5$ | Mg | 2.5 |
| Vitamin $B_6$ | Mg | 2.5 |
| Vitamin $B_9$ | Mcg | 500 |
| Vitamin $B_{12}$ | Mcg | 5 |
| Vitamin C | Mg | 150 |
| Vitamin $D_3$ | IU | 1000 |
| Vitamin E | IU | 100 |
| Vitamin $K_1$ | Mcg | 25 |
| Vitamin $K_2$ | Mcg | 50 |
| Boron | Mg | 2.5 |
| Calcium | Mg | 500 |
| Chromium Picolinate | Mcg | 500 |
| Iron | Mg | 15 |
| Magnesium | Mg | 400 |
| Selenium | Mcg | 100 |
| Zinc | Mg | 15 |
| Vanadium | Mcg | 5 |
| Omega-3 | Mg | 5 |
| Omega-6 | Mg | 15 |
| Omega-9 | Mg | 15 |
| Coenzyme $Q_{10}$ | Mg | 100 |
| Super CitriMax | Mg | 150 |
| L-Carnitine | Mg | 150 |
| Optional Fenugreek or Xanthan Gum | Mg | 10 |
| Optional Erythritol | G | 5 |
| Color | mL | 0.01 |
| Flavor | mL | 0.01 |
| Total Volume | mL | ~250 |

All or some of the components from the "Other - E" group below may be combined with some or all of the components of Mixture A.

Mixture A has a deep maroon-red color and a faint fruity flavor. Further information regarding the ingredients is provided as follows:

Acaiberry

Scientific Name: *Euterpe oleracea* (FIG. A-1)

Acaiberry is high in antioxidants, vitamins, minerals and contains omega 6 and 9 fatty acids, which are associated with heart health.

Nutrient analysis results from 100 grams of powder yields 533.9 calories, 52.2 grams carbohydrates, 8.1 grams protein and 32.5 grams total fat. The carbohydrate portion includes 44.2 grams of dietary fiber. Acai contains high levels of the monounsaturated fatty acid oleic acid (56.2% of total fats). It is also rich in palmitic acid (24.1% of total fats, a saturated fat) and the polyunsaturated omega-6 fatty acid linoleic acid (12.5% of total fats). β-sitosterol (beta-sitosterol), a phytosterol that competes with dietary cholesterol for absorption and so may reduce blood cholesterol levels.

Goji/Wolfberry

Scientific Name: *Lycium barbarum* (FIG. A-2)

Goji helps stimulate the release of gGH—"youth hormone" and helps to reverse the age-related decline of IgA, an essential immune protein. This can result in an improved immune response, memory, healthy metabolism, sexual energy and anti-flammatory enzyme (SOD). It contains many nutrients and phytochemicals including: 11 essential and 22 trace dietary minerals; 18 amino acids; 6 essential s; 8 polysaccharides and 6 monosaccharides; 5 unsaturated fatty acids, including the essential fatty acids, linoleic acid and alpha-linolenic acid; beta-sitosterol and other phytosterols; 5 carotenoids, including beta-carotene and zeaxanthin, lutein, lycopene and cryptoxanthin, xanthophyll; numerous phenolic pigments.

Seaberry

Scientific Name: *Hippophae rhamnoides* (FIG. A-3)

Known as Seabuckthorn or Seaberry may be one of the plant world's most nutritious foods. It has extensive nutrient and phytochemical diversity, including one of the highest vitamin C and E contents, extraordinary pulp and seed levels of alpha linolenic, oleic, palmitic, palmitoleic and linoleic fatty acids, carotenoids and phenolics. Beautifully orange-colored Seaberry is rich in various lipids, natural vitamin A, vitamin C, vitamin $B_1$, vitamin $B_2$, vitamin $B_6$, vitamin E, vitamin F, vitamin P, vitamin K, carotenoids, sugars, minerals, organic acids, irreplaceable amino acids, microcells and other bioactive compounds with nutritional and medicinal properties.

Mangosteen

Scientific Name: *Garcinia mangostana* (FIG. A-4)

Over 40 different Xanthones have been found in Mangosteen, which are chemically beneficial molecules, each molecule has remarkable properties. These free radical scavenger/fighters stop pain, reduce swelling and inflammation, and help in the body's healing process. The "strong" antioxidants strengthen cells, kill bacteria, viruses, fungus, and stop the attack in DNA and even have restorative properties. They help the body run as a complete, interrelated and integrated system. They help the mind think better, adapt better, and give a sense of well-being (anti-depressant). They stop the damage of brain cells so they grow and divide properly and help the cells and the neuro-transmitters function properly. They aid with Alzheimer's disease, and all forms of memory loss. They help in the battle against degenerative diseases like cancer, heart disease, diabetes, arthritis, and all forms of brain malfunctions. They help the vision process: cataracts, macular degeneration, glaucoma, and other forms of vision loss may be prevented. By controlling free radicals, antioxidants can make the difference between life and death, as well as influence how fast and how well we age.

Black Currants

Scientific Name: *Ribes nigrum* (FIG. A-5)

Black Currants has more vitamin C than any other fruit and are the highest in the antioxidant called anthocyanins. The anthocyanins in Black Currants have shown to be beneficial in warding off ailments including heart disease, cancer, Alzheimer's disease, diabetes and high blood pressure.

Black Carrot

Scientific Name: *Daucus carota* (FIG. A-6)

Black Carrots contain anthocyanins, part of the flavonoid antioxidant family. Flavonoids may be used as anticancer compounds, as well as inhibitors of LDL (the bad) cholesterol. It has anti-bacterial and anti-fungicidal properties.

Grapes

Scientific Name: *Vitis vinifera, Vitis labrusca, Vitis rotundifolia* (FIG. A-7)

North American grapes (*Vitis labrusca* and *Vitis rotundifolia*): Varieties include Concord (blue-black in color and large in size), Delaware (pink-red in color with a tender skin) and Niagara (amber colored and less sweet than other varieties). North American varieties feature skins that more easily slip away from their flesh.

European grapes (*Vitis vinifera*): Varieties include Thompson (seedless and amber-green in color), Emperor (seeded and purple in color) and Champagne/Black Corinth (tiny in size and purple in color). European varieties feature skins that adhere closely to their flesh.

Grapes contain beneficial compounds called flavonoids, which are phytonutrients that give the vibrant purple color to grapes, grape juice and red wine; the stronger the color, the higher the concentration of flavonoids. These flavonoid compounds include quercitin, as well as a second flavonoid-type compound (falling into the chemical category of stilbenes) called resveratrol.

In addition to resveratrol and saponins, grapes contain yet another compound called pterostilbene, powerful antioxidants that are already known to fight cancer and may also help lower cholesterol.

Researchers have found not only an increase in blood antioxidant activity, but also discovered that grape juice protected LDL cholesterol from oxidation, a phenomenon that can turn LDL into an artery-damaging molecule. Although LDL is often called the "bad" form of cholesterol, it becomes harmful when damaged by free radicals or "oxidized."

Additionally, it was found that phenolic compounds in grape skins inhibit protein tyrosine kinases, a group of enzymes that play a key role in cell regulation. Compounds inhibiting these enzymes that suppress the production of a bad protein causing blood vessels to constrict hence it reduces the flow of oxygen to the heart. This bad protein, called endothelin-1, is thought to be a key contributing agent in the development of heart disease.

Concord grapes have the highest and broadest range of polyphenols and the highest overall antioxidant capacity. The main components in purple grape juice were flavan-3-ols, anthocyanins, and hydroxycinnamates, together accounting for 93% of the total phenolic content.

Muscadine grapes (*V. rotundifolia*) have high levels of antioxidants and they have more functional genes than wine grapes and therefore provides higher levels of ellagic, OPC's, quercetin, anthocyanidins and resveratrol compounds. These compounds make Muscadine Grape seed a potent antioxidant.

Pomegranate

Scientific Name: *Punica granatum* (FIG. A-8)

It is among a novel category of exotic plant sources called superfruits. Providing 16% of an adult's daily vitamin C requirement per 100 milliliters serving, pomegranate juice is also a good source of the B vitamin, pantothenic acid, potassium and antioxidant polyphenols. The most abundant polyphenols in pomegranate juice are the hydrolyzable tannins called punicalagins shown to have potent free-radical scavenging ability in laboratory studies. Antioxidant punicalagins absorb into the human body after consumption of pomegranate extracts, and an ex-vivo study of human plasma after consumption of a pomegranate extract standardized to punicalagins indicated an average 32% increase in plasma antioxidant capacity.

Furthermore, pomegranate extracts have no sugar, calories, or additives. Many pomegranate extracts are essentially ellagic acid which absorb into the body after parent molecules, punicalagins are hydrolyzed.

In preliminary laboratory research, pomegranate has been found effective in reducing heart disease risk factors, including LDL oxidation, macrophage oxidative status, and foam cell formation, all of which are steps in atherosclerosis and cardiovascular disease. Tannins such as punicalagins have been identified as the primary components responsible for the reduction of oxidative stress which led to these risk factors. Pomegranate has been shown to reduce systolic blood pressure by inhibiting serum angiotensin-converting enzymes. Interim reports released to the public media were that pomegranate juice may slow the onset or development of prostate cancer.

Containing polyphenols which inhibit estrogen synthesis, pomegranate seed oil was effective against the proliferation of breast cancer cells in vitro. The juice may also have antiviral and antibacterial effects against dental plaque.

Blueberry

Scientific Names: *Vaccinium* spp. (*Vaccinium angustifolium, Vaccinium boreale, Vaccinium caesariense*) (FIG. A-9)

Researchers have shown that blueberry anthocyanins, proanthocyanidins, flavonols and tannins inhibit mechanisms of cancer cell development in vitro. It may alleviate the cognitive decline occurring in Alzheimer's disease and other conditions of aging.

Animal studies found that blueberry consumption lowered cholesterol and total blood lipid levels, possibly affecting symptoms of heart disease, stroke and altered glycosaminoglycans, vascular cell components that can influence control of blood pressure.

One cup (145 g) of blueberry provides 31% of the dietary reference intake for vitamin C, 16% for dietary fiber, 20% for manganese and 7% for vitamin E, with a low glycemic load.

Tart Cherry

Scientific Name: *Prunus cerasus* (FIG. A-10)

Tart cherry powder made from whole tart cherries may help maintain a healthy cardiovascular system and also fight cell oxidative stress (cell damage caused by free radicals). Tart cherries may offer protection against heart disease, Type-2 diabetes and memory loss.

Bitter Melon

Scientific Name: *Momordica charantia* (Synonyms: *Momordica chinensis, Momordica elegans, Momordica indica, Momordica operculata, Momordica sinensis, Sicyos fauriei*) (FIG. A-11)

It contains four very promising bioactive compounds. These compounds activate a protein called AMPK, which is well known for regulating fuel metabolism and enabling the glucose uptake processes which are impaired in diabetics. It may be useful for preventing and treating malaria and HIV. Sabinsa (www.sabinsa.com) Corporation has a commercial water soluble Bitter Melon.

Jamun

Scientific Name: *Syzygium cumini* (FIG. A-12)

Common Names: Eugenia Jambolana, Plum, Black Plum, Jaman, Jambolan

The fruit has a combination of sweet, mildly sour, astringent flavor and tends to color the tongue purple. The seed is also used to control diabetes, and is a good source of vitamin A and vitamin C. The quantitative determination showed that *Syzygium cumini* seeds contained 40% of water soluble gummy fibre and 15% of water insoluble neutral detergent fibre (NDF) and found that the soluble gummy fibre isolated from *Syzygium cumini* seeds significantly lowered blood glucose levels and improved oral glucose tolerance.

Turmeric

Scientific Name: *Curcuma longa* (FIG. A-13)

Turmeric may be a remedy for Diabetes. It is more effective if taken with an equal amount of Amla powder. Curcumin extract is one of the major antioxidants in turmeric. Through these antioxidants, Turmeric—Curcumin helps maintain a healthy cardiovascular, a healthy neuroprotective system and a healthy digestive/colon system. It may be possible to dissolve Turmeric and/or Curcumin powder in oil and/or an emulsifier like Lecithin and then adding water to the "Turmeric or Curcumin powder and oil/emulsifier mixture"—such a mixture may be ready for dissolving with other ingredients. It may be also possible to utilize Sabinsa (www.sabinsa.com) Corporation's Curcumin derivatives—Tetrahydrocurcuminoid.

Moreover, Curcumin and/or its derivatives have poor bioavailability. However, Curcumin may be encapsulated via a micro-emulsion or nano-emulsion method utilizing ethyl oleate, lecithin and Tween 80 as the oil phase and surfactants respectively. When the mole ratio of Lecithin to Tween 80 was 0.3, the optimum capacity of oil solubility was reached at 10.3% by weight. However, natural Curcumin has low bioavailability and quickly loses its attributes when ingested. Adding black pepper (*Piper nigrum* or *Piper longum*) to Curcumin may boost its absorption. Curcumin with a substance found in cruciferous vegetables like cauliflower and/or broccoli can reduce the growth of prostate tumor cells more effectively than when they're used alone.

Out of many variations of Curcumin molecules, it was found that GO-Y030 and GO-Y031 molecules are more potent and bioavailable.

Whey, Soy or Rapeseed Protein (FIG. A-14)

Whey protein helps control blood glucose levels and has been shown to be beneficial for weight management, both of which are often a concern for Type-2 diabetes. University of Kentucky's meta-analysis concluded that soy protein is correlated with significant decreases in serum cholesterol, Low Density Lipoprotein LDL (bad) cholesterol and triglyceride concentrations. However, High Density Lipoprotein HDL (good) cholesterol did not increase. Water soluble Rapeseed (Canola), Soy or Whey protein is a good choice for Type-2 diabetes.

Secoisolariciresinol Diglycoside (SDG) Lignans (FIG. A-15)

Scientific studies show that flax lignans support cardiovascular function, prostate health, bone health, healthy cell replication and hormone balance. Recent study suggests the utility of SDG lignans for cardiovascular health, particularly with impaired glycemic control. Secoisolariciresinol diglucoside (SDG) from flaxseed has been shown to be effective in preventing/delaying the development of Type-1 and Type-2 diabetes. The hypoglycemic effect of SDG in Type-2 diabetes has been suggested to be due to its antioxidant activity. Hyperglycemia in Type-2 diabetes could be due to an increase in the expression of phosphoenolpyruvate carboxykinase (PEPCK), a rate-limiting enzyme in the gluconeogenesis in the liver. It is possible that the hypoglycemic effect of SDG in Type-2 diabetes is due to suppression of expression of PEPCK genes. The results suggest that SDG suppresses the expression of PEPCK genes and that the hypoglycemic effect may be due to suppression of PEPCK gene expression.

Salba

Scientific Name: *Salvia hispanica* (FIG. A-16)

It is a whole grain that is rich in fiber, alpha-linolenic acid (ALA), and minerals.

Salba has more heart-healthy and memory boosting Omega 3's of 3,050 mg, beneficial dietary fiber of about 5000 mg, six times more bone-building calcium than whole milk and fifteen times more magnesium than broccoli per serving.

Sprouted Flaxseed

Scientific Name: *Linum usitatissimum* (FIG. A-17)

Sprouted Flaxseed has many health benefits. Sprouting doubles the antioxidant (ORAC) value of flaxseed. Nutrients such as enzymes, amino acids, and vitamins are substantially increased and become more bioavailable, allowing for better absorption. The "anti-nutrients" such as phytic acid, enzyme inhibitors and insoluble fibers are decreased.

Micro-Nutrients (FIG. A-18)

Vitamin A, vitamin $B_3$ (NADH), vitamin $B_5$, vitamin $B_6$, vitamin $B_{12}$, vitamin C, vitamin $D_3$, vitamin E, vitamin $K_1$, vitamin $K_2$, Boron, Calcium, Iron, Magnesium, Selenium, Vanadium, Zinc, Omega-3, Omega-6, Omega-9 and Coenzyme $Q_{10}$. Moreover, nano-dispersed/nano-sized vitamin and nano-dispersed/nano-sized minerals can enhance bioavailability. Furthermore, vitamin $B_3$ (NADH) may have moderate benefits against depression, Parkinson's and Alzheimer's diseases. Furthermore, vitamin A and vitamin C may also be added. These micro-nutrients may be encapsulated within a Calcium Phosphate shell or an engineered liposome or a chitosan biopolymeric nano-particle for higher bioavailability.

Super CitriMax® (FIG. A-19)

Super CitriMax® curbs appetite, burns fat and results in significant weight loss without side effects; it also promotes healthy blood lipid levels and reduces Body Mass Index, an indicator of healthy body weight. It has been shown to increase levels of serum serotonin, a neurotransmitter involved in mood, sleep and appetite control, which may help address many of the emotional issues overweight people face, including binge-eating and depression.

Hydroxy Citric Acid (HCA) (FIG. A-20)

*Garcinia cambogia* is a small fruit that resembles a miniature pumpkin. The extract from its fruit and rind is popular in many natural weight loss products. The extract is hydroxycitric acid (HCA), claimed to suppress appetite and enhance fat-burning.

The theory behind that HCA inhibits an enzyme called citrate lyase that helps turn excess carbohydrates into fat. By inhibiting this enzyme, it is believed the body instead boosts carbohydrate oxidation, or simply put, burns the extra carbs. In extensive animal studies, *Garcinia cambogia* was found to reduce food intake by suppressing appetite, as well as to decrease body fat.

L-Carnitine (FIG. A-21)

Two studies found that supplementing aged rats with either L-Carnitine or alpha-lipoic acid (ALA), improved mitochondrial energy metabolism, decreased oxidative stress, and improved memory.

Fenugreek Gum (FIG. A-22)

It has been confirmed by animal experiments and clinical tests on humans that ingesting food compounded with fenugreek gum powder lowers the level of sugar in the blood. Moreover, fenugreek seeds lower the level of cholesterol and fat in the blood and restrains biosynthesis of cholesterol in the liver. These effects are caused by galactomannan contained in albumen in seeds (fenugreek gum). Polysaccharide, or dietary fiber, generally has the effect of lowering the level of cholesterol, and fenugreek is distinctive for having the effect of lowering the level of sugar in the blood as well.

Erythritol (FIG. A-23)

Erythritol is a naturally-derived sugar substitute that looks and tastes very much like sugar, yet has almost no calories. It comes in granulated and powdered forms. It is absorbed into the bloodstream in the small intestine, before it enters the large intestine, it does not normally cause laxative effects as are often experienced after over-consumption of other sugar alcohols and most people can consume Erythritol with no side effects without causing gastric distress.

Example 2

Mixture B

| All or some of the components of Mixture(s) A and/or C may be combined with some or all of the components of the following: | | |
|---|---|---|
| Grape Seed | Mg | 75 |
| *Aloe vera* | Mg | 50 |
| Orange Peel | Mg | 30 |
| Wheatgrass | G | 3.5 |
| Resveratrol/Resvida ®/Resvenox ® | Mg | 10 |
| Optional Piracetam ® | Mg | 800 |

All or some of the components from the "Other - E" group below may be combined with some or all of the components of Mixture B.

Grape Seed

Scientific Name: *Vitis vinifera, Vitis rotundifolia, Vitis labrusca* (FIG. B-1)

Grape seed extract contains chemicals known as polyphenols, (including the subclass of proanthocyanodins), which are recognized to be effective polyphenol antioxidants.

Grape seed extract may help to prevent and treat heart diseases such as high blood pressure and high cholesterol. By limiting oxidation, antioxidants in grape seed extract may help prevent changes, including damage to blood vessels that may contribute to the development of heart disease. Substances in grape seed extract may also block the effects of enzymes that process fats, including cholesterol from the diet. Consequently, less fat may be absorbed and more may be eliminated from the body. Other research shows that grape seed extract may help to prevent or control damage to body cells that is caused by toxins.

*Aloe Vera*

Scientific Name: *Aloe vera* (FIG. B-2)

*Aloe vera* is also called as *Aloe barbadensis*. It has a remarkable anti-viral property via a compound called acemannon. The anti-viral action of acemannon was found to extend even to transformation of the protein envelope of the HIV virus—thus preventing it from attaching to cells. However, these results are preliminary. In another study carried out by Lee Cowden at Dallas, Tex., it was seen that regular oral consumption of *Aloe vera* benefited several disorders of the gastrointestinal tract like irritable bowl syndrome, ulcerative colitis, esophagitis, peptic ulcer, rheumatoid arthritis, osteoarthritis, mouth lesions, sore throat, and lupus. In another study carried out by R. H. Davis at the University of Pennsylvania, it was observed that *Aloe vera* can prevent and arrest arthritis, inhibit pain, reduce inflammation and restore bone growth.

Lee et al., at the Department of Food and Nutrition, Ho Seo University, Korea have isolated a strong antioxidative compound from a methanolic extract of *Aloe barbadensis*. The investigators found that the antioxidative action of the compound isolated from Aloe extract was of a comparable efficacy as that of alpha-tocopherol.

Pugh and Ross at the Department of Pharmacognosy, National Centre for Natural Products Research, University of Missisippi, have characterized a new immunostimulatory polysaccharide called Aloeride from commercial *Aloe vera* (*Aloe barbadensis*). The investigators observed that Aloeride induced the expression of the mRNAs encoding IL-1beta and TNF-alpha to levels equal to those observed in cells maximally activated by LPS. According to the investigators, aloeride although just 0.015% of the aloe juice dry weight has a remarkable action on activation of macrophages and may be the single most important component of *Aloe vera* juice.

Orange Peel

Scientific Name: *Citrus sinensis* (FIG. B-3)

A class of compounds found in citrus fruit peels called polymethoxylated flavones (PMFs) have the potential to lower cholesterol more effectively than some prescription drugs, and without any side effects, according to a study by U.S. and Canadian researchers that was published in the Journal of Agricultural and Food Chemistry.

Sweet orange oil consists of about 90% d-Limonene which is known as a significant chemopreventive anti-cancer agent. The phytonutrient d-limonene is found abundantly in the peels of oranges and studies show that d-limonene may reduce the risk of some cancers.

The most important flavanone in oranges, hesperidin has been shown to lower high blood pressure as well as cholesterol in animal studies, and to have strong anti-inflammatory properties. Most of the phytonutrient is found in the peel and inner white pulp of the orange, rather than in its liquid orange center.

Wheat Grass

Scientific Name: *Triticum aestivum* (FIG. B-4)

It is rich in Chlorophyll, Beta Carotene, Minerals & Live enzymes. An example of Nutrients: Wheat Grass of 30 grams is given below:

| Nutrient | Wheat Grass Juice |
| --- | --- |
| Protein | 860 mg |
| Beta carotene | 120 IU |
| Vitamin E | 880 mcg |
| Vitamin C | 1 mg |
| Vitamin $B_{12}$ | 0.30 mcg |
| Phosphorus | 21 mg |
| Magnesium | 8 mg |
| Calcium | 7.2 mg |
| Iron | 0.66 mg |
| Potassium | 42 mg |

Resveratrol (FIG. B-5)

Resveratrol (trans-3,5,4'-trihydroxystilbene) is a substance found in the skins of certain red grapes, in peanuts, blueberry, some pines and giant knotweed. Resveratrol is produced by grapes and other plants to protect the plant against fungus, and disease. Resveratrol at low doses can retard some aspects of the aging process, including heart aging, and it may do so by mimicking some of the effects of caloric restriction, which is known to retard aging in several tissues and extend life span.

DSM (www.dsm.com) Corporation is manufacturing a synthetic resveratrol product called Resvida®. Sabinsa (www.sabinsa.com) Corporation is manufacturing a synthetic resveratrol product called Resvenox®. For example: natural Resveratrol and synthetic Resveraterol e.g., Resvida® or Resvenox® will be considered as a similar component.

Generally both natural Resveratrol and synthetic Resveraterol has a poor solubility in water, but their solubility in water can be improved by premixing with a food-grade ethanol and a food-grade propylene glycol. Furthermore, a food-grade short-chain triglyceride (SCT) e.g., triceprylin, a food-grade medium-chain triglyceride (MCT) e.g., coconut oil, a food-grade glycerine oil and an emulsifier e.g., Tween 20 and Tween 80 can be utilized to manufacture a micro-emulsified or a nano-emulsified Resveratrol. The above chemicals can also act as a partial solvent in extracting botanical properties from a component derived from any part of a seed or a root or a rhizome, or a leaf or a fruit or fruit skin or a vegetable or a vegetable skin or plant bark.

Piracetam® (FIG. B-6)

Piracetam® is a cyclic derivative of GABA and it is nootropic. It is a dietary supplement which is claimed to enhance cognition and memory, slow down brain aging, Alzheimer's disease, increase blood flow/oxygen to the brain, and aid stroke recovery.

Example 3

Mixture C

| All or some of the components of Mixture(s) A and/or B may be combined with some or all of the components of the following: | | |
| --- | --- | --- |
| Gardenia | mL | 75 |
| Indian Kino Tree | Mg | 450 |
| Guduchi | Mg | 250 |
| Gurmar | Mg | 400 |
| Cinnamon | Mg | 750 |
| Fenugreek | G | 2.5 |

| All or some of the components of Mixture(s) A and/or B may be combined with some or all of the components of the following: | | |
| --- | --- | --- |
| Clove | Mg | 100 |
| Fennel | Mg | 450 |

All or some of the components from the "Other - E" group below may be combined with some or all of the components of Mixture C.

Gardenia
  Scientific Name: *Gardenia jasminoides* (FIG. C-1)
  Gardenia fruit extract which may be used in to treat symptoms of Type-2 diabetes and contains a chemical that reverses some of the pancreatic dysfunctions that underlie the disease.
  The primary active components of gardenia are iridoid glycosides (mainly geniposide and gardenoside), chlorogenic acid, and ursolic acid. Gardenia extract contains the chemical called "genipin." This Genipin stimulates the secretion of insulin in control but not a UCP2-deficient pancreas. Acute addition of genipin to isolated pancreatic tissue reversed high glucose and obesity induced dysfunction of insulin-producing beta cells. A derivative of genipin that lacked the chemical's cross-linking activity continued to inhibit UCP2.

Indian Kino Tree
  Scientific Name: *Pterocarpus marsupium* (FIG. C-2)
  Common Names: Indian Kino Tree, Malabar Kino Tree, Kino
  *Pterocarpus marsupium* is an anti-diabetic plant indigenous to South India. Mechanisms such as the stimulating or regenerating effect on beta cells or extrapancreatic effects are proposed for the hypoglycemic action of the Indian Kino Tree extract. The isoflavone from *Pterocarpus marsupium* may activate glucose transport, improving glucose uptake in the body and is quite similar to insulin in its action. Administration of *Pterocarpus marsupium* led to a decrease in blood glucose levels by 38% and 60% on the 15th and 30th day of the experiment.

Guduchi
  Scientific Name: *Tinospora cordifolia* (FIG. C-3)
  Guduchi is bitter, pungent and astringent in taste, sweet in the post digestive effect, hot in potency and has a special potency as an anti-toxin. Oral administration of the extract of *Tinospora cordifolia* roots for 6 weeks resulted in a significant reduction in blood and urine glucose and in lipids in serum and tissues in alloxan diabetic rats.

Gurmar/Periploca of the Woods
  Scientific Name: *Gymnema sylvestre* (FIG. C-4)
  It may be used in an all natural medication for diabetes with other ingredients such as Cinnamon, Chromium (Chromium Picolinate), Zinc, Biotin, Banaba, Huckleberry and Bitter Melon. Extracts of Gymnema is used for treatment of hyperglycemia, obesity, high cholesterol levels, anemia and digestion. The active ingredient is thought to be gurmenic acid which is useful against obesity. Gymnemic acids delay glucose absorption in the blood.
  When Gymnema leaf extract is administered to a diabetic patient, there is stimulation of the pancreas by virtue of an increase in insulin release. Some possible mechanisms by which the leaves and especially Gymnemic acids from *Gymnema sylvestre* exert its hypoglycemic effects are:
    It increases secretion of insulin.
    It promotes regeneration of islet cells.
    It increases utilization of glucose: it is shown to increase the activities of enzymes responsible for utilization of glucose by insulin-dependant pathways, an increase in phosphorylase activity, decrease in gluconeogenic enzymes and sorbitol dehydrogenase.

It causes inhibition of glucose absorption from the intestine.

The leaves are also noted for lowering serum cholesterol and triglycerides.

Cinnamon

Scientific Name: *Cinnamomum zeylanicum, Cinnamomum cassia blume* (FIG. C-5)

Cinnamon's flavor is due to an aromatic essential oil which makes up 0.5% to 1% of its composition. Chemical components of the essential oil include ethyl cinnamate, eugenol, cinnamaldehyde, beta-caryophyllene, linalool and methyl chavicol. Recent research has revealed that constituents in cinnamon bark called procyanidin Type-A polymers help maintain the body's ability to metabolize glucose in a healthy way. Cinnamon also contains calcium, iron, vitamins and fiber. However, *Cinnamomum zeylanicum* is preferred over *Cinnamomum cassia blume* due to its low Coumarin content.

Fenugreek

Scientific Name: *Trigonella foenum-graecum* (FIG. C-6)

Fenugreek is used both as an herb (the leaves) and as a spice (the seed). Supplements of fenugreek seeds were shown to lower serum cholesterol, triglyceride, and low-density lipoprotein in human patients and experimental models of hypercholesterolemia and hypertriglyceridemia. Several human trials have demonstrated the anti-diabetic effect of its seeds. It is often cited as a natural remedy for migraines, blood pressure and LDL blood cholesterol levels.

Clove

Scientific Name: *Syzygium aromaticum* (FIG. C-7)

Extracts of cloves were found to improve the function of insulin and to lower glucose, total cholesterol, LDL and triglycerides in people with Type-2 diabetes.

Clove extract acts like insulin in hepatocytes and hepatoma cells by reducing phosphoenolpyruvate carboxykinase (PEPCK) and glucose 6-phosphatase (G6 Pase) gene expression. Much like insulin, clove-mediated repression is reversed by PI3K inhibitors and N-acetylcysteine (NAC).

Fennel

Scientific Name: *Foeniculum vulgare* (FIG. C-8)

Fennel contains anethole, which acts as phytoestrogens—an herbal composition for the treatment of diabetes.

Example 4

Mixture D

| All or some of the components of Mixture(s) A, B, and/or C may be combined with some or all of the components of the following: | | |
| --- | --- | --- |
| Extracts of (Black, White & Green Tea) | Mg | 250-1000 |
| *Coccinia indica* | Mg | 250-1000 |
| *Salacia oblonga* | Mg | 250-1000 |
| Resistance Starch | G | 3.5 |
| Diachrome ™ | Mcg | 500 |
| InsuVital ™ | Mg | 5 |
| Pycnogenol ® | Mg | 50 |
| Biotin | Mcg | 5-30 |
| Beta-Glucan | Mg | 30-500 |
| Conjugated Linoleum Acid (CLA) | G | 3 |
| Alpha-Lipoic Acid (ALA) | Mg | 600 |
| SX-Fraction | Mg | 70 |

All or some of the components from the "Other - E" group may be combined with some or all of the components of Mixture D.

For pH balance Citric, Malic, Fumaric, and Tartaric acid(s) may be added. Also preservatives such as Sodium Benzoate, Potassium Sorbate and/or Disodium EDTA may be added.

Decaffeinated Tea (Black, Green & White)

Scientific Name: *Camellia sinensis* (FIG. D-1)

Black, Green and White tea polyphenols have been found to be potent inhibitors of amylase. Just one cup of green tea was found to inhibit 87% of amylase's activity. And if less sugar gets into the bloodstream, blood glucose levels will automatically be lowered.

Ivy Gourd

Scientific Name: *Coccinia indica* (FIG. D-2)

*Coccinia indica* may reduce blood sugar levels by about 20 percent. One gram daily dose of *Coccinia indica* extract may result an 18% reduction in blood sugar levels after meals, according to a double blind, placebo controlled, randomized study.

*Salacia*

Scientific Name: *Salacia oblonga* (FIG. D-3)

*Salacia oblonga* contains two potent a-Glucosidase inhibitors: Salicinol and Kotalanol 9. *Salacia oblonga* has also been found to show inhibitory activity on Aldose Reductase which is related to diabetic complications as peripheral neuropathy, retinopathy, and cataracts. *Salacia oblonga* is an effective anti-diabetic and dieting agent. 2.5 to 5.0 grams of *Salacia oblonga* daily is effective in lowering blood glucose, serum cholesterol, triglycerides and increasing the HDL cholesterol levels in Type-2 diabetics.

Resistant Starch (FIG. D-4)

Resistant starch has been categorized into four types:

Physically inaccessible or digestible resistant starch, such as that found in seeds or legumes and unprocessed whole grains Resistant starch that occurs in its natural granular form, such as uncooked potato, green banana flour and high amylose corn Resistant starch that is formed when starch-containing foods are cooked and cooled such as in bread, cornflakes and cooked-and-chilled potatoes or retrograded high amylose corn Starches that have been chemically modified to resist digestion. This type of resistant starches can have a wide variety of structures and are not found in nature Resistant starch is a starch that escapes digestion in the small intestine of healthy individuals. Resistant starch is considered the third type of dietary fiber, as it can deliver some of the benefits of insoluble fiber and some of the benefits of soluble fiber.

Some carbohydrates, such as sugars and most starch are rapidly digested and absorbed as glucose into the body through the small intestine and subsequently used for short-term energy needs or stored. Resistant starch, on the other hand, resists digestion and passes through to the large intestine where it acts like dietary fiber.

Diachrome™ (FIG. D-5)

Diachrome™ (patented composition of chromium picolinate and biotin). It not only improves blood sugar levels, but decreases LDL cholesterol which will help people with diabetes in lowering LDL cholesterol.

InsuVital™ (FIG. D-6)

InsuVital™ consists of extensively hydrolysed casein, a protein which is present in milk. A proprietary enzyme has been used to cut ("hydrolyse") the casein into smaller pieces, also called peptides. The mixture of peptides of 2 or 3 amino acids forms the active part of InsuVital™. These peptides can stimulate the secretion of insulin from the pancreas, even in people suffering from Type-2 diabetes.

Pine Tree

Scientific Name: *Pinus maritima* (FIG. D-7)

Pine Tree extracts such as commercially available Pycnogenol® or Toyo-FVG provides significant health protection in diabetes which caused the lowering of glucose levels and improvements in microvascular health problems such as diabetic microangiopathy, foot ulcer healing, muscle cramps, prevention and improvement of diabetic retinopathy.

For example: Pycnogenol®, Toyo-FVG® and any *Pinus maritima* extracts will be considered as the same (not distinct) components.

Biotin (FIG. D-8)

Biotin, also known as vitamin H or $B_7$, has the chemical formula $C_{10}H_{16}N_2O_3S$. People with type 2 diabetes often have low levels of biotin. Biotin may be involved in the synthesis and release of insulin. Preliminary studies in both animals and people suggest that biotin may help improve blood glucose control in those with diabetes, particularly Type-2 diabetes. Specifically, biotin doses in excess of nutritional requirements lower postprandial glucose and improve glucose tolerance.

Beta-Glucan (FIG. D-9)

Beta Glucan stimulates the immune system by activating the macrophage cells, powerful, immune cells that engulf foreign invaders and alert the body's other defenses. By increasing the activity of the macrophage cells, the immune system is thereby made stronger and better able to fight off foreign invaders and health challenges.

Conjugated Linoleum Acid (FIG. D-10)

Conjugated Linoleum Acid (CLA) may protect against development of diabetes, atherosclerosis, chronic inflammation and colon cancer. It is found predominantly in dairy products such as milk, cheese and meat, and are formed by bacteria in ruminants that take linoleic acids—fatty acids from plants—and convert them into Conjugated Linoleum Acid.

Alpha-Lipoic Acid (FIG. D-11)

Alpha-lipoic acid (ALA) is a vitamin-like substance that helps to make energy in your body. As an antioxidant, it is used to treat acquired immunodeficiency syndrome (AIDS).

Several studies suggest that treatment with alpha-lipoic acid may help reduce pain, burning, itching, tingling, and numbness in people who have nerve damage (called peripheral neuropathy) caused by diabetes. Alpha-lipoic acid speeds the removal of glucose (sugar) from the blood of people with diabetes and that this antioxidant may prevent kidney damage associated with diabetes in animals.

Because alpha-lipoic acid can pass easily into the brain, it has protective effects on brain and nerve tissue and shows promise as a treatment for stroke and other brain disorders involving free radical damage. Animals treated with alpha-lipoic acid, for example, suffered less brain damage and had a four times greater survival rate after a stroke than the animals who did not receive this supplement. While animal studies are encouraging, more research is needed to understand whether this benefit applies to people as well.

Seed oils are the richest sources of alpha-lipoic acid, notably those of rapeseed (canola), soybeans, walnuts, flaxseed (Linseed), perilla, chia and hemp. Alpha-lipoic acid is also obtained from the thylakoid membranes of the green leaves of broadleaf plants (the membranes responsible for photosynthesis). Chia (*Salvia hispanica*), Kiwi (*Actinidia chinensis*), Perilla (*Perilla frutescens*), Flax (*Linum usitatissimum*), Lingonberry (*Vaccinium vitis-idaea*), Purslane (*Linum usitatissimum*), Seaberry (*Hippophae rhamnoides*) has 64%, 62%, 58%, 55%, 49%, 35% and 32% alpha-lipoic acid respectively.

SX-Fraction (FIG. D-12)

Maitake SX fraction is safe and is very helpful for Type-2 diabetes. Studies on SX-Fraction have been conducted at Georgetown University and New York Medical College respectively over the last two years. The results show that SX-Fraction does indeed possess a more potent ability to enhance insulin sensitivity for controlling blood sugar levels and lowering blood pressure than X-fraction.

OTHER—E

The following ingredients can be included in any of mixture(s) A, B, C and/or D above.

Acerolaberry

Scientific Name: *Maldighia glabra* (FIG. E-1)

Acerolaberry is cultivated for its high vitamin C content and the juice contains 32 times the amount of vitamin C in orange juice (over 3000% as much).

Alfalfa

Scientific Name: *Medicago sativa* (FIG. E-2)

Alfalfa contains calcium, potassium, iron, zinc, protein and vitamins A, $B_1$, $B_6$, C, E, and K. It is high in chlorophyll, helps to lower cholesterol and reduces arterial plaque. It helps against arthritis, rheumatism, coliits, ulcers, anemia, frequent nose bleeds, diabetes, and osteoporosis.

Arhat

Scientific Name: *Siraitia grosvenorii* (FIG. E-3)

*Siraitia grosvenorii* is 300 times sweeter than sugar. It has some medicinal properties for heat stroke, chronic infection, chronic cough, constipation and diabetics.

Astaxanthin (FIG. E-4)

Astaxanthin is a carotenoid. Its potent antioxidants may be beneficial in cardiovascular, immune, inflammatory, oxidative damage and neurodegenerative diseases such as glaucoma and Alzheimer's.

Bael

Scientific Name: *Aegle marmelos* (FIG. E-5)

Common Names: Bael, Quince, Apple Wood, Holy Fruit Tree

Leaves are scientifically proved to be anti-diabetic. Drinking fresh juice of leaves daily along with a pinch of black pepper will take care of some excess body sugar.

Baobab

Scientific Name: *Adansonia digitata* (FIG. E-6)

The baobab fruit pulp contains up to 56% water soluble pectins by weight. The fruit has been used to treat dehydration and lower elevated body temperatures without having an effect on normal body temperatures.

Bazzein & Pentadin

Scientific Name: *Pentadiplandra brazzeana* (FIG. E-7)

Bazzein is a sweet-tasting (2000 times sweeter than sugar) monomer protein, consisting of 54 amino acid residues extracted from the fruits of the Oubli plant. As a protein it is safe for diabetics and very soluble in water. It can withstand heat for any food manufacturing process. Bazzein is isolated from the fruit of Pentadiplandra brazzana Baillon, a plant found in West Africa. Brazzein consists of a single chain of 54 amino acid residues and no carbohydrates.

Pentadin is a (1000 times sweeter than sugar) monomer protein extracted also from fruits of Oubli plant.

Cabbage

Scientific Name: *Brassica oleracea* (FIG. E-8)

A recent study reveals the anti-diabetic effects of cabbage. This is as effective as high doses of Insulin. It is a low calorie, anti-cancer, fiber filled food that lowers excess sugar naturally.

Cedarberry
   Scientific Name: *Juniperus monosperma* (FIG. E-9)
   Cedarberry can help regulate both low and high blood sugar conditions.

Chongcao
   Scientific Name: *Cordyceps sinensis* (FIG. E-10)
   Common Names: Cordyceps Mushroom, Caterpillar Fungus, Chongcao, Deer Fungus Parasite, Dong Chong Xia Cao and Chong Cao.
   Chongcao is helpful in reducing high cholesterol and improving male function. It fights against stress, controls blood sugar levels, lowers blood pressure and reduces cancer risk.

Cocoa Extract
   Scientific Name: *Theobroma cacao* (FIG. E-11)
   Flavonoid-rich cocoa powder has a favorable effect on LDL ("bad" cholesterol). Flavonoids found in chocolate include the flavanols, notably epicatechin, catechin and proanthocyanidins.

Custard Apple Leaf
   Scientific Name: *Annona reticulata* (FIG. E-12)
   A recent study revealed that newly emerged leaves of long pepper lowers blood sugar levels effectively.

Curculin (FIG. E-13)
   Curculin is a sweet protein from the fruit of *Curculigo latifolia* (Hypoxidaceae). It is heat unstable and it makes sour solutions taste sweet.

Damiana Extract
   Scientific Name: *Turnera diffusa* (FIG. E-14)
   Damiana extract can treat asthma, depression, digestive problems, menstrual disorders and various forms of sexual dysfunction.

Dandelion Root
   Scientific Name: *Taraxacum officinale* (FIG. E-15)
   Dandelion root is a rich source of vitamins A, B, C and D, iron, lecithin, silicon, potassium, magnesium, zinc and manganese. It enhances liver and gall bladder functions. It aids sugar regulation through liver cleansing. It may also decrease high blood pressure due to its diuretic properties.

Elecampane Leaf
   Scientific Name: *Inula helenium* (FIG. E-16)
   Elecampane leaf contains a soluble fiber named Inulin, which aids in blood sugar control. Its roots can be used to treat pnuemonia, coughs and bronchitis.

Gac
   Scientific Name: *Momordica cochinchinensis* (FIG. E-17)
   Gac is high in lycopene content. Relative to mass, it contains up to 70 times the amount of lycopene found in tomatoes. It has been found to contain up to 10 times the amount of beta-carotene of carrots and sweet potatoes. Additionally, the carotenoids present in Gac are bound to long-chain fatty acids, resulting in what is claimed to be a more bioavailable form. There has also been recent research that suggests that Gac contains a protein that may inhibit the proliferation of cancer cells.

Ginsengberry
   Scientific Name: *Panax quinquefolium* (FIG. E-18)
   Ginsengberry's active compounds are dammarane saponins, also known as ginsenosides. It enhances stamina and reduces fatigue and physical stress.

Glycine (FIG. E-19)
   Glycine is an amino acid which can help to regulate both low and high blood sugar conditions. It may prove effective in conditions associated with memory and cognitive behavior as well.

Guar Gum
   Scientific Name: *Cyamopsis tetragonolobus* (FIG. E-20)
   It refers to a guaran or galactomannan. It is primarily the ground endosperm of guar beans. The guar seeds are dehusked, milled and screened to obtain the guar gum.
   Guar gum is of interest with regards to both weight loss and diabetic diets. This weight loss is thought to be a function of its high soluble fiber content. Guar gum was found to improve dietary glucose tolerance. Research has revealed the water soluble fiber in guar gum may help people with diabetes by binding with glucose in the gastrointestinal tract, thus preventing its absorption. Guar gum gives a sense of fullness after eating therefore it is good for obesity.

Hawthomeberry
   Scientific Name: *Crataegus oxyacantha* (FIG. E-21)
   Hawthomeberry has vitamin C, flavonoids (quercetin and quercetrin), glycosides, proanthocyanidins, anthocynaidins, saponins, tannins, and cratetegin. It can help support the arterial walls, dilate (enlarge) coronary blood vessels (the vessels supplying the heart with vital oxygen, blood, and nutrients), maintain cholesterol levels, aid digestion and strengthen the heart's pumping ability.

Huereque
   Scientific Name: *Ibervillea sonorae* (FIG. E-22)
   Huereque is beautifully adapted to survival in its arid habitat. It stores reserves of water and food that can be drawn upon during dry seasons. Its roots can be used to treat diabetes.

Indian Beech
   Scientific Name: *Pongamia pinnata* (FIG. E-23)
   Common Names: Indian Beech, Poongam oil tree, Honge, Ponge. Flowers are useful in diabetes. Oral administration of ethanolic extract of the *Pongamia pinnata* flower shows significant anti-hyperglycemic, anti-lipid per-oxidative effect and enhancement in antioxidant defense.

Indian Gentian
   Scientific Name: *Swertia chirata* (FIG. E-24)
   Common Names: Clearing Nut Tree, Bitter Stick, Chirette Indian, Dowa I Pechish, Indian Gentian. Indian gentian contains xanthones and amarogentin, a glycoside.
   The ethanolic extract of Swertia chirayita exhibits hypoglycemic activity. The hexane fraction containing swerchirin, the main hypoglycemic principle, induced a significant fall in blood sugar in albino rats. The compound may have clinical applications in the control of diabetes Indian Gooseberry
   Scientific Name: *Phyllanthus emblica* (Also known as *Emblica officinalis*) (FIG. E-25)
   Indian gooseberry has in-vitro antiviral and antimicrobial properties. Experimental preparations of leaves bark or fruit have shown potential efficacy against bad blood cholesterol, cancer, age-related renal disease and diabetes. The fruit also contains tannis, polyphenols, flavonoids, kaempferol, ellagic acid and gallic acid.

Kudzu
   Scientific Name: *Pueraria lobata, Pueraria thomsonii* (FIG. E-26)
   Kudzu has useful isoflavones, including daidzein (an anti-inflammatory and antimicrobial agent), daidzin (a cancer preventive) and genistein (an antileukemic agent). Kudzu has a unique source of the isoflavone puerarin.
   The compounds from Kudzu root can affect neurotransmitters (including serotonin, GABA and glutamate). These compounds may treat alcohol-cravings, migraine, allergies, diarrhea, post-menopausal symptoms, hypertension and diabetes Type-2.

Licorice Weed
   Scientific Name: *Scoparia dulcis* (Synonyms: *Scoparia grandiflora, Scoparia ternata, Capraria dulcis, Gratiola micrantha*) (FIG. E-27)
   Also known as: Vassourinha, ñuñco pichana, anisillo, bitterbroom, boroemia, broomweed, brum sirpi, escobilla, mastuerzo, piqui pichana, pottipooli, sweet broom, tapixava and tupixaba.
   Licorice weed contains the phytochemicals flavone and terpene, which are responsible for its biological properties. Methanol extract of vassourinha leaves also showed toxic actions against cancer cells (with a 66% inhibition rate).
Loquat
   Scientific Name: *Eriobotrya japonica* (FIG. E-28)
   Loquat leaves contain corosolic acid, clinically proven to activate facilitative glucose transporters within the cell to utilize glucose more efficiently. Corosolic acid is clinically proven to activate cell glucose-transporter "shuttles" and thus helps balance blood glucose levels. Corosolic acid shows a memory effect of blood glucose lowering even after the treatment is stopped.
Lychee
   Scientific Name: *Litchi chinensis* (FIG. E-29)
   Fruit has a sweet odor of rose and traditionally the fruits are said to be used as antioxidant tonic to heart, brain, liver, and thirst and are very wholesome to the body. Various natural products are available for the treatment of liver disorders.
Mabinlin
   Scientific Name: *Capparis masaikai* (FIG. E-30)
   Mabinlins are sweet-tasting proteins extracted from the seed of Mabinlang, a Chinese plant growing in Yunnan province. Mabinlin is a soluble and heat stable protein. Its high heat stability makes it more suitable used as a sweetener.
Marionberry
   Scientific Name: *Rubus ursinus* (FIG. E-31)
   Marionberry has an exceptional aroma and taste. It is a rich source of antioxidants, vitamin A, vitamin C and fibres. Moreover, it has phenolic acids which are known as potent anti-carcinogenic agents.
Miraculin
   Scientific Name: *Synsepalum dulcificum* or *Richadella dulcifica* (FIG. E-32)
   Miraculin is a soluble and heat stable protein glycoprotein extracted from the miracle fruit plant. It is not sweet by itself, but it can change a sour beverage into a sweet beverage. It may change the structure of taste cells on the tongue.
Monellin
   Scientific Name: *Dioscoreophyllum cumminsii* (FIG. E-33)
   Monellin is a sweet (1000 times sweeter than sugar) heat unstable (?) protein extracted from the fruit of serendipity-berry.
Onion Family (Onion Garlic, Scallion and Leeks)
   Scientific Classification: Liliaceae Family (FIG. E-34)
   Two sets of compounds make up the majority of onion's known active constituents-sulfur compounds, such as allyl propyl disulphide (APDS), and flavonoids, such as quercetin. Each of these groups of compounds has multiple medicinal actions. APDS has been shown to block the breakdown of insulin by the liver and possibly to stimulate insulin production by the pancreas, thus increasing the amount of insulin and reducing sugar levels in the blood.
   Garlic is also alleged to help regulate blood sugar levels. Regular and prolonged use of therapeutic amounts of aged garlic extracts lower blood homocysteine levels, and has shown to prevent some complications of diabetes mellitus.

Phyllanthus Plant
   Scientific Name: *Phyllanthus niruri* (FIG. E-35)
   Common Names: Phyllanthus Plant, Child Pick-a-back, Gulf Leafflower, Black Catnip, Meniran, Chanca Piedra, Shatterstone, Stone Breaker, Quebra Pedra, Gale Of Wind, Carry Me Seed, Creole Senna, Daun Marisan.
   Phyllanthus Plant helps prevent jaundice, diabetes, dyspepsia, ulcers, sores, swellings, ophthalmia and chronic dysentery.
Prickly Pear
   Scientific Name: *Opuntia ficus-indica* (FIG. E-36)
   Prickly Pear is a rich source of flavanoids, including kaempferol, quercetin, kaempferol 3-methyl ether, quercetin 3-methyl ether, narcissin, dihydrokaempferol (aromadendrin, 6), dihydroquercetin and eriodictyol. These flavanoids are responsible for Prickly Pear's health enhancing benefits and can protect the immune system and prevent oxidative stress by acting as a free radical scavenger. The antioxidant action can protect cells and organs. The amino acids, fiber and B3 (niacin) prevent excess blood sugar conversions into fats, while reducing the total cholesterol, triglyceride, LDL cholesterol levels by metabolizing fat and fatty acids and eliminating excess bile acids (excess bile acid is eventually converted into cholesterol). Other research studies on B3 (niacin) show its conversion effects of LDL (bad) to HDL (good) forms of cholesterol and help decrease the risk of heart disease.
Ranawara or Avaram
   Scientific Name: *Cassia auriculata* (FIG. E-37)
   This plant is said to contain a cardiac glucoside (sennapicrin), sap, leaves and bark yield contain oxymethylanthraqunone while the latter contains tannins. The root can be used against fevers, diabetes, diseases of the urinary system and constipation.
Sarsaparilla
   Scientific Name: *Smilax officinalis* (FIG. E-38)
   Sarsaparilla contains plant steroids. The absorption of other drugs and photochemicals are attributed to these plant steroids that can be synthesized into human steroids such as estrogen and testosterone. Its flavonoids have immune modulation and liver protective activities.
   It also contains cortin hormone. The human body will die almost immediately if this hormone is stopped but if there is insufficient amount, the human body becomes easily ill and develops nervous depression and general weakness.
Stevia
   Scientific Name: *Stevia rebaudiana* (FIG. E-39)
   Common Names: Sweet Leaf, Sugar Leaf, Sweet Honey Leaf, Rebiana. Stevia (also known as *Eupatorium rebaudianum* Bertoni) is known simply as Stevia or Sutebia or Satiwia.
   Stevia is an all-natural sweetener that contains no chemicals and is 250 times sweeter than sugar but has none of the calories, and it can be used as sugar. Rather than raise blood sugar like most other natural sweeteners, Stevia actually lowers it. Stevia helps control blood glucose and promotes insulin creation. As a sugar substitute, it has a slower onset/longer duration than that of sugar. Results of the study led the researchers at the time to conclude that the plant extract Stevioside may potentially be used as a new medication for Type-2 diabetes.
Suma Root
   Scientific Name: *Pfaffia paniculata* (FIG. E-40)
   Suma root contains 19 different amino acids, many electrolytes, trace minerals (iron, magnesium and zinc), vitamins A, $B_1$, $B_2$, E, K, pantothenic acid and a high amount of germanium. The root contains novel phytochemicals including saponins, pfaffic acids, glycosides and nortriterpenes. It helps to regulate blood sugar and provide energy. It also enhances energy and the immune system.

Thaumatin

Scientific Name: *Thaumatococcus daniellii* (FIG. E-41)

Thaumatin is a low-calorie & heat stable protein sweetener and flavor modifier. It is a mixture of proteins isolated from the katemfe fruit (*Thaumatococcus daniellii* Bennett). The substance is often used primarily for its flavor modifying properties and not exclusively as a sweetener.

The thaumatins were first found as a mixture of proteins isolated from the katemfe fruit (*Thaumatococcus daniellii*). Some of the proteins in the thaumatin family are natural sweeteners roughly 2000 times more potent than sugar. Although very sweet, thaumatin's taste is markedly different from sugar. The sweetness of thaumatin builds very slowly. Perception lasts a long time leaving a liquorice-like aftertaste at high usage levels. Thaumatin is highly water-soluble, and stable to heating and stable under acidic conditions.

Tulsi

Scientific Name: *Ocimum sanctum, Ocimum tenuiflorum* (FIG. E-42)

Tulsi is helpful in a significant reduction in total cholesterol levels and blood glucose levels due to its antioxidant properties.

Water Hyssop

Scientific Name: *Bacopa monnieri* (FIG. E-43)

Water Hyssop can treat for epilepsy and asthma. The extracts of the plant improve memory capacity, motor learning ability, antianxiety effect, cognitive ability. It can reduce oxidation of fats in the bloodstream.

Walnuts

Scientific Name: *Juglans regia* (FIG. E-44)

It is high in antioxidants, ALA (an omega-3 fatty acid) and arginine. It can keep beta-amyloid protein in a soluble form and preventing the breakdown of acetylcholine, both of which could delay the onset of Alzheimer's disease.

Other Ingredients

Astaxanthin, Avocado/Soybean Unsaponifiables, Beta-Carotene, Catechin, Chlorella, Chondroitin sulfate, Cognizin® (Citicoline), Cyanidin, Diindolylmethane, D-Ribose, Epigallocatechin Gallate, Fruitful®, Gamma-Linolenic Acid, GanedenBC30™, GliSODin® (Superoxide Dismutase), Glucosamine, Hesperidin, Indole-3-Carbinol, Kaempferol, L-Analyl-L-Glutamine, Lecithin, Lipowheat™, 5-Loxin™, Lutien, Lycopene, Myricetin, Naringenin, Oligonol®, OptiMSM®, Oregano extract, Pantothenic acid, Pelargonidin, Phospholipid Phosphatidylserine, Piceatannol, Pterostilbene, Quercetin, Rutin, S-Adenosylmethionine, Setria® (Glutathione), SkinGestPSOR™, Sulforaphane and Suntheanine® (L-Theanine).

Preservative

HerBev®, nano-sized silver particles, Rosemary (*Rosmarinus officinalis*), Seaberry (*Hippophae rhamnoides*) and T-50 vitamin E oil.

Other Plant Ingredients

Algae Spirulina (*Arthrospira platensis*), Almond (*Amygdalus communis*), Amla (*Phyllanthus emblica*), Apple (*Malus domestica*), Apricot (*Prunus armeniaca*), Araca-Boi (*Eugenia stipitata*), Artichoke (*Cynara scolymus*), Aronia (*Aronia melanocarpa*), Ashwagandha (*Withania somnifera*), Avocado (*Persea gratissima*), Baical (*Scutellaria baicalensis*) Barley Grass (*Hordeum vulgare*), Beet (*Beta vulgaris*), Bilberry (*Vaccinium myrtillus*), Blackberry (*Rubus villosus*), Black Johannisberry (*Genes ribes*), Boysenberry (*Rubus ursinus x idaeus*), Broccoli (*Brassica oleracea italica*), Broccoli Rabe (*Brassica rapa*), Cabbage (*Brassica oleracea var. capitata*), Camu-Camu (*Myrciaria dubia*), Cantaloupe (*Cucumis melo*), Carrot (*Daucus carota*), Chamomile (*Chamaemelum nobile*), Cherimoya (*Annona cherimola*), Cherry (*Prunus cerasu*), Chili (*Rosa Roxburghii*), Chinese Goldthread (*Coptis chinensis*), Cheonkung (*Cnidium officinale*), Choriyanam (*Tragia involucrata*), Coconut (*Cocus nucifera*), Coffeeberry (*Rhamnus californica*), Cowitch (*Mucuna pruriens*), Cranberry (*Vaccinium macrocarpon*), Cupuacu (*Theobroma grandiflorum*), Dragon Fruit (*Hylocereus undatus*), Elderberry (*Sambucus nigra*), Gac (*Momordica cochinchinensis*), Ginger (*Zingiber officinalis*), Ginseng (*Panax ginseng*), Golden Root (*Rhodiola rosea*), Graviola (*Annona muricata*), Grapefruit (*Citrus paradisi*), Guarana (*Paullinia cupana*), Guava (*Psidium guajava*), Guavasteen (*Feijoa sellowiana*), Hu Zhang (*Polygonum cuspidatum*), Indian Kudzu (*Pueraria tuberosa*), Jiaogulan (*Gynostemma pentaphyllum*), Juniper (*Juniperus communis*), Kiwi (*Actinidia chinensis*), Lemon (*Citrus limonum*), Lingonberry (*Vaccinium vitis-idaea*), Loganberry (*Rubus loganobaccus*), Lulo (*Solanum quitoense*), Maitake Mushroom (*Grifola frondosa*), Maralu (*Rhaponticum carthamoides*), Marking Nut Tree (*Salacia reticulata*), Milk Thistle (*Silybum marianum*), Mulberry (*Morus alba/rubra/nigra*), Mulberry (*Morus alba/rubra/nigra*) With 1-deoxynojirimycin (DNJ), Nectarine (*Prunus persica*), Neem (*Azadirachta indica*), Noni (*Morinda citrifolia*), Olive (*Oleae europaea*), Orange (*Citrus aurantium*), Paddle Weed (*Ecklonia cava*), Papaya (*Carica papaya*), Passion Flower (*Passiflora incarnate*), Passion Fruit (*Passiflora edulis*), Pepper (*Piper nigrum*), Persimmon (*Diospyros virginia*), Pineapple (*Ananas comosus*), Pinyin (*Schisandra chinensis*), Plum (*Prunus umbellate*), Prune (*Prunus domestica*), Quebracho (*Aspidosperma quebracho*), Quince (*Cydonia oblonga*), Raisins (*Vitis vinifera*), Raspberry (*Rubus idaeus*), Rhubarb (*Rheum rhabarbarum*), Rosehip (*Rosa rubiginosa*), Siberian Chaga (*Inonotus obliquus*), Spinach (*Spinacia oleracea*), Soy (*Glycine max*), Strawberry (*Fragaria virginiana*), Tangerine (*Citrus reticulate*), Tarragon (*Artemisia dracunculus*), The Creat (*Andrographis paniculata*), Tomato (*Solanum lycopercicum*), Watercress (*Nasturtium officinale*), Yohimbe (*Pausinystalia johimbe*), Yumberry (*Myrica rubra*) and Yuzu (*Citrus ichangensis x C. reticulata*).

For example: *Morus alba, Morus rubra* & *Morus nigra* are the same species of Morus family.

Preparation Under Inert Gases

The ingredients of Mixtures A, B, C, D and E may be heated at about 90° C. for about 4 seconds under any food-grade inert gas(s) such as nitrogen and/or argon or any combination thereof to reduce microbial contamination, nutritional degradation and oxidation.

Nano-Dispersion

Reactants: low-bioavailable ingredient (e.g., Catechin, Coenzyme $Q_{10}$, Quercetin, Resveratrol and Superoxide Dismutase), an emulsifier and water move at about 5 meters/second through separate flow channels, they converge on each other for hundreds of milliseconds and macro-mix occurs. Next, this macro-mixture moves downstream and splits into separate flow channels of narrower (about 40 micron) diameters. In the process, the macro-mixture is accelerated to velocities at about 50 meters/second for tens of milliseconds and meso-mixing occurs. Next this meso-mixture moves downstream and splits into separate flow channels of narrowest (about 10 micron) diameters. Furthermore, the meso-mixture is accelerated to extremely high velocities to collide and micro-mixing occurs—thus creating a nano-dispersion of low-bioavailable ingredient.

Nano-Emulsion

Non-water soluble ingredient e.g. Curcumin can be dissolved in sunflower oil. Reactants: the oil solution, an emulsifier and water move at about 5 meters/second through separate flow channels, they converge on each other for hundreds of milliseconds and macro-mix occurs. Next, this macro-mixture moves downstream and splits into separate flow channels of narrower (about 40 micron) diameters. In the process, the macro-mixture is accelerated to velocities at about 50 meters/second for tens of milliseconds and meso-mixing occurs. Next this meso-mixture moves downstream and splits into separate flow channels of narrowest (about 10 micron) diameters. Furthermore, the meso-mixture is accelerated to extremely high velocities to collide and micro-mixing occurs—thus creating a nano-emulsion of non-water soluble ingredient.

Nano-Encapsulation

Low-bioavailable ingredient (e.g., Catechin, Coenzyme $Q_{10}$, Quercetin, Resveratrol and Superoxide Dismutase) can be encapsulated by chitosan, chitosan/modified lecithin, cyclodextrin, dendrimer, liposome, milk protein and plant protein (e.g., zein plant proteins). Chitosan nano-particles may stick to the intestinal wall for antioxidants to be absorbed. Cyclodextrin and dendrimer are like microscopic balls with a dense network of branches. Cyclodextrin and dendrimer have an incredibly high surface area to volume ratio and they can diffuse nutrients into the blood slowly over time. Similarly, aroma, flavor, low-bioavailable minerals, low-bioavailable vitamins can also be encapsulated.

FIG. F-1 shows a picture of cyclodextrins. A cyclodextrin is a circular sugar ring molecule. Once water is added to cyclodextrin, cyclodextrin forms a cavity to hold an ingredient. Cyclodextrin spreads out and enhances bioavailability of the ingredient by significantly enhancing the surface area.

FIG. F-2 shows a method of encapsulation of an ingredient (100) within a glycolipid nanotube (120) in water solution (140).

FIG. F-3 shows a method of encapsulation of an ingredient (100) within a nano-vessel (160) such as Calcium Phosphate or an engineered liposome or a chitosan biopolymer.

Antioxidant (solution or nano-dispersed) can be deposited on an inactive yeast for thermal/heat stability above 90° C. Antioxidant-on-yeast can be incorporated into a biscuit, a cooking oil, a lozenge, a nutritional bar and a yogurt.

Personalized Nutrition

A user can analyze genes that can influence how he or she processes certain nutrients for certain risk factors and diseases. With encoded user's gene profile on a gene card, the user can insert this gene card into a "gene-smart" read-out module and receive a customized list of personalized nutrition profile and/or prepared nutrition. FIG. F-4 shows a block diagram of an apparatus (180) that comprises an instant "gene-smart" insert module (200), a "gene-smart" sequencer module (220), a micro-processor module (240), a "gene-smart" print-out module (260), a "gene-smart" read-out module (280) and a personalized nutrition mixing/preparation module (300).

Example 5

Super Antioxidant Formulation

| | | |
|---|---|---|
| Coconut Water | mL | 225 |
| Mangosteen | mL | 12.5 |
| Kiwi or Lychee or Pineapple | mL | 12.5 |
| Extracts of [Amla, Bilberry, Blueberry, Grape, Pine Bark, Pomegranate & Tea] | Mg | 1000 |
| Extracts of [Apple, Aronia/Chokeberry, Black Currant, Blueberry, Carrot, Elderberry, Hibiscus and Lemon] | Mg | 1000 |
| Nano-Encapsulated Superoxide Dismutase | Mg | 150 |
| Glutathione | Mg | 50 |
| Nano-Encapsulated Coenzyme Q10 | Mg | 150 |
| Nano-Encapsulated Resveratrol | Mg | 150 |
| Nano-Encapsulated Qucertine | Mg | 150 |
| Lycopene | Mg | 150 |
| Indole-3-Carbinol | Mg | 300 |
| Nano-Dispersed Plant Sterols | Mg | 500 |
| Vitamin A | IU | 1000 |
| Vitamin $B_3$ | Mg | 15 |
| Vitamin $B_5$ | Mg | 2.5 |
| Vitamin $B_6$ | Mg | 2.5 |
| Vitamin $B_9$ | Mcg | 500 |
| Vitamin $B_{12}$ | Mcg | 5 |
| Vitamin C | Mg | 150 |
| Vitamin $D_3$ | IU | 1000 |
| Nano-Emulsified Vitamin E | IU | 100 |
| Vitamin $K_1$ | Mcg | 25 |
| Vitamin $K_2$ | Mcg | 50 |
| Boron | Mg | 2.5 |
| Calcium | Mg | 500 |
| Chromium Picolinate | Mcg | 500 |
| Nano-Dispersed Iron | Mg | 15 |
| Magnesium | Mg | 400 |
| Selenium | Mcg | 100 |
| Zinc | Mg | 15 |
| Vanadium | Mcg | 5 |
| Omega-3 | Mg | 5 |
| Omega-6 | Mg | 15 |
| Omega-9 | Mg | 15 |
| Nano-Encapsulated/Nano-Dispersed Curcumin | Mg | 50 |
| Stevia | Mg | 50 |
| Erythritol | Mg | 7500 |
| Color | mL | 0.01 |
| Flavor | mL | 0.01 |
| Total Volume | mL | ~250 |

The above detailed description is to illustrate the specific best-mode embodiment of the present invention, but it is not intended to be limiting. Numerous modifications are possible within the scope of the present invention. The present invention is set forth in the accompanying claims.

What is claimed is:

1. A supplement consisting of:
    a) any ten components selected from the group consisting of alpha lipoic acid, astaxanthin, catechin, citicoline, coenzyme Q10, conjugated linoleic acid, cyanidin, diindolylmethane, gamma-linolenic acid, glutathione, glycine, hesperidin, indole-3-carbinol, kaempferol, L-theanine, lycopene, myricetin, naringenin, pelargonidin, phosphatidylserine, piceatannol, plant sterols, pterostilbene, quercetin, resveratrol, rutin, S-adenosylmethionine, sulforaphane and superoxide dismutase;
    b) at least five components selected from the group consisting of: *Andrographis paniculata, Azadirachta indica, Bacopa monnieri, Cinnamomum zeylanicum, Cnidium officinale, Coccinia indica, Crataegus oxyacantha, Curcuma longa, Gymnema sylvestre, Juglans regia, Momordica charantia, Mucuna pruriens, Ocimum sanctum, Panax ginseng, Panax quinquefolium,*

*Paullinia cupana, Pfaffia paniculata, Phyllanthus emblica, Phyllanthus niruri, Pinus maritima, Polygonum cuspidatum, Prunus cerasus, Punica granatum, Salacia oblonga, Scutellaria baicalensis, Silybum marianum, Syzygium cumini, Tinospora cordifolia, Trigonella foenum-graecum* and *Withania somnifera*; and c) one or more components encapsulated within an encapsulant selected from the group consisting of: chitosan, a cyclodextrin, a dendrimer, a lecithin, a liposome, and a plant protein, wherein said one or more components encapsulated within the encapsulant is selected from the group consisting of an antioxidant, a component recited in a), a component recited in b), an enzyme, an enzymatic antioxidant, and a vitamin.

2. A supplement comprising:

a) at least ten components selected from the group consisting of alpha lipoic acid, astaxanthin, catechin, citicoline, coenzyme Q10, conjugated linoleic acid, cyanidin, diindolylmethane, gamma-linolenic acid, glutathione, glycine, hesperidin, indole-3-carbinol, kaempferol, L-theanine, lycopene, myricetin, naringenin, pelargonidin, phosphatidylserine, piceatannol, plant sterols, pterostilbene, quercetin, resveratrol, rutin, S-adenosylmethionine, sulforaphane and superoxide dismutase;

b) at least five components selected from the group consisting of: *Andrographis paniculata, Azadirachta indica, Bacopa monnieri, Cinnamomum zeylanicum, Cnidium officinale, Coccinia indica, Crataegus oxyacantha, Curcuma longa, Gymnema sylvestre, Juglans regia, Momordica charantia, Mucuna pruriens, Ocimum sanctum, Panax ginseng, Panax quinquefolium, Paullinia cupana, Pfaffia paniculata, Phyllanthus emblica, Phyllanthus niruri, Pinus maritima, Polygonum cuspidatum, Prunus cerasus, Punica granatum, Salacia oblonga, Scutellaria baicalensis, Silybum marianum, Syzygium cumini, Tinospora cordifolia, Trigonella foenum-graecum* and *Withania somnifera*; and c) one or more components encapsulated within an encapsulant selected from the group consisting of: chitosan, a cyclodextrin, a dendrimer, a lecithin, a liposome, and a plant protein, wherein said one or more components encapsulated within the encapsulant is selected from the group consisting of an antioxidant, a component recited in a), a component recited in b), an enzyme, an enzymatic antioxidant, and a vitamin.

* * * * *